United States Patent [19]
Klessing et al.

[11] Patent Number: 4,965,283
[45] Date of Patent: Oct. 23, 1990

[54] AMINO ACID ESTERS, PROCESS FOR THE PREPARATION THEREOF AND USE THEREOF

[75] Inventors: Klaus Klessing, Ettlingen; Shyam S. Chatterjee, Karlsruhe, both of Fed. Rep. of Germany

[73] Assignee: Dr. Willmar Schwabe GmbH & Co., Karlsruhe, Fed. Rep. of Germany

[21] Appl. No.: 372,640

[22] PCT Filed: Nov. 4, 1988

[86] PCT No.: PCT/DE88/00684
§ 371 Date: Jun. 8, 1989
§ 102(e) Date: Jun. 8, 1989

[87] PCT Pub. No.: WO89/04310
PCT Pub. Date: May 18, 1989

[30] Foreign Application Priority Data
Nov. 4, 1987 [DE] Fed. Rep. of Germany ....... 3737399

[51] Int. Cl.$^5$ ................ C07D 307/60; C07D 405/12; A61K 31/40; A61K 31/365
[52] U.S. Cl. ................................ 514/422; 548/517; 549/318; 514/471
[58] Field of Search ............... 548/517; 549/313, 318; 514/413, 422, 471

[56] References Cited
U.S. PATENT DOCUMENTS
3,541,214 11/1970 Heusser et al. .................... 514/473
4,855,320 8/1989 Chatterjee et al. ................ 514/473

FOREIGN PATENT DOCUMENTS
3615157 12/1987 Fed. Rep. of Germany ...... 514/473

Primary Examiner—Mark L. Berch
Assistant Examiner—Celia Chang
Attorney, Agent, or Firm—Frost & Jacobs

[57] ABSTRACT

Novel esters of amino acids are proposed of which the alcoholic components are formed from threo-4-alkoxy-5-arylhydroxymethyl-2(5H)-furanones. These esters may be present in the form of racemates, pure diastereomers or enantiomers or in the form of diastereomer or enantiomer mixtures. The compounds are anticonvulsive and antiepileptic and due to their good water solubility are easier to administer and more readily absorbable than known anti-convulsives and antiepileptics. A novel process is also disclosed which leads stereoselectively to the diastereomers or the enantiomers or mixtures thereof. The invention further relates to the use of the novel amino acid esters as pharmaceutical preparations and in the production of pharmaceutical preparations.

8 Claims, No Drawings

AMINO ACID ESTERS, PROCESS FOR THE PREPARATION THEREOF AND USE THEREOF

The invention relates to esters of which the acid component is an amino acid radical and the alcoholic component is the radical of a 4-alkoxy-5-arylhydroxymethyl-2(5H)-furanone, that is amino acid esters of the general formula I

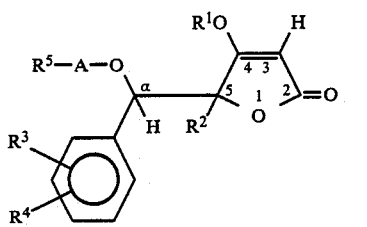

(I)

wherein the oxygen atoms at C-5 and C-α assume relatively to each other the threo position and wherein
$R^1$ is a methyl or ethyl group,
$R^2$ is a hydrogen atom or a methyl group,
$R^3$ and $R^4$ are independently from each other a hydrogen, fluorine, chlorine or bromine atom, a lower alkyl group having 1 to 3 C atoms, a perfluoro lower alkyl having 1 to 3 C atoms, the difluoromethoxy or nitro group,
A is the acyl radical of one of the following amino acids: alanine, leucine, isoleucine, norleucine, valine, norvaline, phenylglycine, phenylalanine, proline, 5-oxoproline, glutamic acid, glutamine, asparaginic acid, asparagine, methionine, glycine, β-alanine, 4-aminobutyric acid, 2-methylalanine or a 1-amino-1-cycloalkane carboxylic acid having a 3-7-member cycloalkyl radical,
in each case a hydrogen atom of the amino group of said amino acids being replaced by the radical $R^5$, and
$R^5$ is a hydrogen atom, a lower alkanoyl radical having 2 to 5 C atoms, the benzyloxycarbonyl radical (Z) or the tert. butoxycarbonyl radical (BOC),
and pharmacologically compatible (acceptable) acid addition salts thereof.

The invention further relates to a process for the preparation of the aforementioned amino acid esters; the latter can be obtained by different combination of the individual process steps as desired in the form of racemates, mixtures of diastereomers or enantiomers or in the form of pure diastereomers or enantiomers. (For the definition of the terms "racemate", "diastereomers" and "enantiomers" cf. Roempps Chemie-Lexikon, 8th Edition, Vol. 2, page 928/929, Franckh'sche Verlagshandlung, Stuttgart 1981).

The invention further relates to pharmaceutical preparations which contain at least one of the compounds according to the invention and to the use of the compounds according to the invention as therapeutic agents and in the treatment of convulsions and diseases of the epileptic group in hot-blooded animals and in humans and the use of said compounds in the preparation of anticonvulsives and antiepileptics.

The compounds of the general formula I contain in their alcoholic component, i.e. the 5-arylhydroxymethyl-2(5H)-furanone substructure, two centres of asymmetry at the carbon atoms C-5 and C-α at which due to the threo configuration of the adjoining oxygen atoms the relative configuration is defined but not the absolute configuration. Consequently, the two following isomers of the general formulae Ia and Ib can occur:

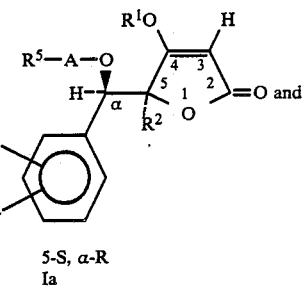

5-S, α-R
Ia

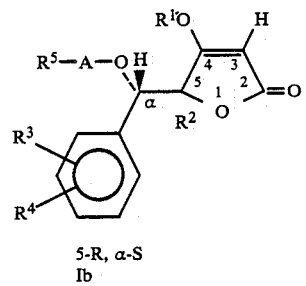

5-R, α-S
Ib

The corresponding erythro compounds with 5-S, α-S and 5-R, α-R configuration are not the subject of this invention.

When the compounds of the general formulae I are esters of an achiral amino acid the isomers Ia and Ib are enantiomeric compounds. If however the compounds of the general formula I are esters of a chiral L- or D-amino acid then (at least) one new centre of asymmetry is added and leads to (at least) 4 diastereomers, that is to (L)-Ia and (L)-Ib as well as (D)-Ia and (D)-Ib, depending on whether L- or D-amino acid is used for the esterification.

The subject of the invention includes all compounds of the general formula Ia, Ib, (L)-Ia, (L)-Ib, (D)-Ia and (D)-Ib and the respective mixtures of Ia with Ib, of (L)-Ia with (L)-Ib and of (D)-Ia with (D)-Ib but not mixtures of L-amino acid esters with D-amino acid esters.

The compounds of the general formula I are novel and are distinguished by anticonvulsive and antiepileptic effectiveness.

A whole number of compounds of very different chemical constitution are known which have anticonvulsive and antiepileptic effectiveness (cf. for example Erhart/Ruschig, Arzneimittel, Vol. 1, p. 177 et seq., Verlag Chemie, Weinheim, 1972), to which belong in particular the active substances carbamazepine, diazepam, diphenylhydantoin, ethosuximide, phenobarbital and valproic acid. All these known anticonvulsives/antiepileptics have chronic-toxic side effects to varying degrees, including exanthema, depressive states, paranoia, megaloblastic anemia, damage to blood-forming bone marrow, liver damage and others. Many of these active substances are sparingly soluble in water; this leads to difficulties in preparing an intravenous or parenteral form of administration and embodies the risk of inadequate bioavailability after oral administration.

There was therefore a need for availability of new pharmaceutical agents with anticonvulsive and antiepileptic effectiveness and at the same time with improved solubility in water and aqueous solvent systems because the physician is only then able to select from a relatively large source of medicaments the agents of which the activity and side-effect spectra best satisfy the physical and psychic needs of the patient.

The problem underlying the invention resides in satisfying this need by making available novel compounds which are more readily soluble in water and have anticonvulsive/antiepileptic effectiveness. The invention is further based on the problem of providing a process for the preparation of such compounds with anticonvulsive/antiepileptic effectiveness with which it is possible to synthesize stereoselectively and specifically the threo compounds of the general formula I in the form of their racemates, diastereomers, enantiomers or their diastereomer or enantiomer mixtures.

The solution of this problem resides in providing and making available the substances according to the invention with convulsive/antiepileptic effectiveness and the pharmaceutical preparations containing said compounds and in the creation of the process according to the invention for preparing the new compounds.

The subject of the invention is in particular the compounds of the general formula I in which the oxygen atoms at C-5 and C-α assume the threo position relatively to each other and in which $R^1$ is a methyl group,
$R^2$ is a hydrogen atom,
one of the two radicals $R^3$ and $R^4$ is a hydrogen atom and the other a fluorine, chlorine or bromine atom located in 2'-position or a methyl or trifluoromethyl group located in 2'-position,
or one of the two radicals $R^3$ and $R^4$ is a fluorine, chlorine or bromine atom or a trifluoromethyl group, respectively in 2'-position, and the other is a chlorine or bromine atom or a trifluoromethyl group, respectively in 4', 5' or 6'-position,
A is the acyl radical of one of the following amino acids: glycine, D or L-alanine, 4-aminobutyric acid, D or L-phenylglycine, D or L-phenylalanine, D or L-proline, D or L-5-oxoproline, D or L-glutamic acid, D or L-glutamine, D or L-methionine, 2-methylalanine or 1-amino-1-cyclohexane carboxylic acid,
a hydrogen atom of the amino group of said amino acids being substituted in each case by the radical $R^5$, and
$R^5$ is a hydrogen atom, a low alkanoyl radical having 2 to 5 C atoms, the benzyloxycarbonyl radical (Z) or the tert. butoxycarbonyl radical (BOC),
and pharmacologically compatible (acceptable) acid addition salts thereof.

Due to their good anticonvulsive/antiepileptic effectiveness the particularly preferred compounds are those of the general formula I in which $R^5$ denotes a hydrogen atom or the low alkanoyl radical having 2 to 5 C atoms.

Further preferred are those compounds of the general formula I in which the amino acid radical, if chiral, has L-configuration.

Finally, particularly preferred are the esters of the general formula I of which the alcoholic component, formed by the threo-5-arylhydroxymethyl-2(5H)-furanone radical, is optically dextrorotary, considered on its own, i.e. is present as (+)-enantiomer.

The invention also relates to a process for preparing the compounds of the general formula I which, depending on the desired substitution pattern as regards the radicals $R^1$, $R^2$, $R^3$, $R^4$, $R^5$ and A and on the desired configuration of the end products, is characterized by one or more of the process steps (A) to (H) described below:

(A) A racemic threo-4-alkoxy-5-arylhydroxymethyl-2(5H)-furanone of the general formula II,

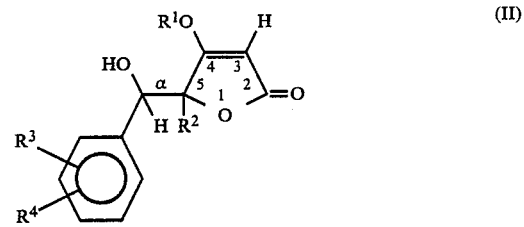

(II)

wherein $R^1$, $R^2$, $R^3$ and $R^4$ have the meanings defined in conjunction with the explanation of the general formula I, is reacted with a reactive amino acid derivative of the general formula III

$R^5$—A—X  (III)

wherein $R^5$ has the meanings defined in conjunction with the explanation of formula I or another protective group for amino groups of amino acids which is usual in peptide chemistry and can be split off acidically or hydrogenolytically, A has the meaning defined in conjunction with the explanation of the general formula I and X is either OH, Cl, Br or the group O—A—$R^5$, the corresponding compound of the general formula I arising in the form of a diastereomer mixture, $R^1$, $R^2$, $R^3$, $R^4$, $R^5$ and A having said meanings.

The radical $R^5$ is always bound to the nitrogen atom of the amino group of the corresponding amino acid, i.e. in the case of the amino acids glutamine and asparagine not to the nitrogen atom of the amide group.

The reactive amino acid derivatives of the general formula III can be amino acids (X=OH) substituted at the amino group by the radical $R^5$, their acid halides (X=Cl, Br) or their acid anhydrides (X=O—A—$R^5$). In the case of glycine for example the following compounds of the general formula III may be involved:
$R^5$—NH—$CH_2$—CO—OH, $R^5$—NH—$CH_2$—CO—Cl (or: —Br) or ($R^5$—NH—$CH_2$—CO)$_2$O.

(B) If a chiral amino acid was used for the esterification in stage (A) the resulting diastereomer mixture can be separated in a manner known per se into the two diastereomers of the general formulae VIIa and VIIb:

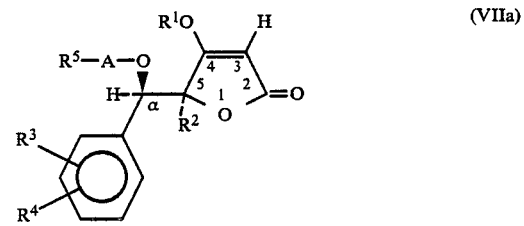

(VIIa)

-continued

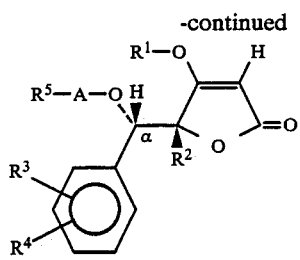
(VIIb)

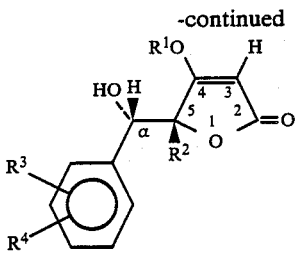
(IIb)

(C) The radical $R^5$, bonded to the nitrogen atom of the amino group, of the amino acid esters obtained in step (A) and/or (B) is split off acidolytically of hydrogenolytically and replaced by a hydrogen atom, resulting in the amino acid esters having a free amino group and being of the general formulae VIII, VIIIa and VIIIb:

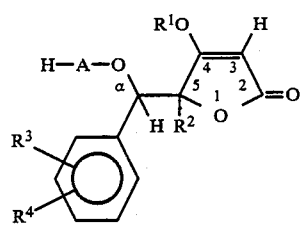
(VIII)

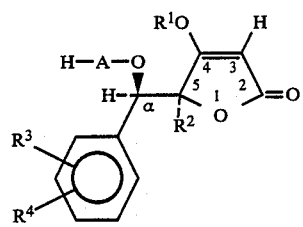
(VIIIa)

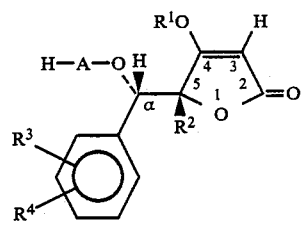
(VIIIb)

(D) If in step (A) a chiral amino acid was used and in particular if the diastereomer separation in step (B) was not carried out or not carried out completely, the mixture of the diastereomers VIIIa and VIIIb is separated into the individual components.

(E) The diastereomeric esters of the general formulae VIIIa and VIIIb are saponified separately from each other to form the enantiomeric furanones of the general formulae IIa and IIb

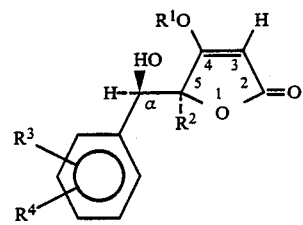
(IIa)

(F) The individual enantiomers of the general formulae IIa and IIb are esterified analogously to step (A) with an achiral amino acid derivative which is protected at the amino group by the radical $R^5$ and has the general formula III $$R^5-A-X \qquad (III)$$

to give compounds of the general formulae VIIa and VIIb which in this case are enantiomers.

(G) The compounds of the general formulae VIIa and VIIb are cleaved analogously to step (C) with splitting off of the radical $R^5$, which is replaced by a hydrogen radical, to give the amino acid esters having a free amino group and the general formulae VIIIa and VIIIb, being in this case enantiomers.

(H) The compounds of the general formulae VIII, VIIIa or VIIIb obtained in step (C) or (G) are reacted with a reactive acyl derivative of the general formulae $$R^5-Y \text{ or } R^5-O-R^5$$

wherein Y denotes a chlorine or a bromine atom and $R^5$ denotes a low alkanoyl radical having 2 to 5 C atoms, or with a ketene of the formula $R^7=C=O$, wherein $R^7$ is an alkylidene radical having 1 to 4 carbon atoms, giving compounds of the general formulae I, Ia or Ib wherein $R^5$ denotes a low alkanoyl radical having 2 to 5 C atoms.

The process according to the invention can be represented schematically by the following flow chart in which the Roman numerals denote the compounds according to the correspondingly designated general formulae and the capital letters in brackets correspond to the correspondingly denoted process steps:

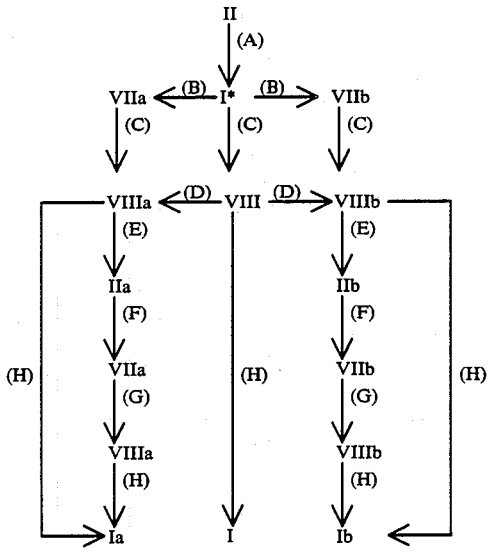

The process according to the invention permits the preparation of all compounds which come under the general formula I, selectively in the form of racemates, pure diastereomers and enantiomers or in the form of mixtures of diastereomers or enantiomers depending on the combination of the process steps chosen. Hereinafter the different combination possibilities of the steps (A) to (H) for preparing the particular compounds desired ("target compounds") of general formula I will be explained in detail:

Case 1: The target compound is a racemate or a diastereomer mixture of a compound of the general formula I, wherein $R^1$, $R^2$, $R^3$, $R^4$, $R^5$ and A have the meanings described at the beginning. It suffices to use for the preparation thereof either (a) only the step (A) when N-protected amino acid derivatives $R^5$—A—X of the general formula III are used which as protective group already have the $R^5$ radical which is also intended for the target compound, with the provision that $R^5$ is not hydrogen ($R^5 \neq H$); or (b) only the steps (A) and (C) if in the target compound $R^5 = H$; or (c) only the steps (A), (C) and (H) if in the target compound the radical $R^5$ is not hydrogen and is different from the radical $R^5$ used as amino protective group in step (A).

Case 2: The target compounds are the individual diastereomers of the general formulae Ia and Ib, wherein $R^1$, $R^2$, $R^3$, $R^4$ and $R^5$ have the meanings described at the beginning and A is the acyl radical of one of the chiral D or L-amino acids described at the beginning. It suffices to use for the preparation either (a) the steps (A) and (B) if $R^5 \neq H$, or (b) the steps (A), (B) and (C) or the steps (A), (C) and (D) if $R^5 = H$, or (c) the steps (A), (B), (C) and (H) or the steps (A), (C), (D) and (H) if $R^5 \neq H$ and $R^5$ is different from the radical $R^5$ used as amino protective group in step (A).

Case 3: The target compounds are the individual enantiomers of the general formulae Ia and Ib, wherein $R^1$, $R^2$, $R^3$, $R^4$ and $R^5$ have the meanings described at the beginning and A is the acyl radical of one of the achiral amino acids described at the beginning. It suffices to use for the preparation either (a) the steps (A), (B), (C), (E) and (F) or the steps (A), (C), (D), (E) and (F) if in step (F) an amino acid derivative of the general formula III is used in which $R^5 \neq H$ or (b) the steps (A), (B), (C), (E), (F) and (G) or the steps (A), (C), (D), (E), (F) and (G) if $R^5 = H$, or (c) the steps (A), (B), (C), (E), (F), (G) and (H) or the steps (A), (C), (D), (E), (F), (G) and (H) if $R^5 \neq H$ and is different from the radical $R^5$ used as amino protective group in step (F).

In all the embodiments of case 3 in step (A) a chiral D or L-amino acid derivative of the general formula III must be used in order to be able to carry out via the steps (B) to (E) a racemate splitting to form the compounds of the general formulae IIa and IIb; the achiral amino acid contained in the target compound need not be introduced until step (F) of the process, i.e. until the furanones of the general formulae IIa and IIb are already present in enantiomeric form and are separate from each other.

Case 4: Target compounds are compounds of the general formula I wherein $R^1$, $R^2$, $R^3$ and $R^4$ has the meanings described at the beginning, $R^5 = H$ and A denotes the acyl radical of D or L-5-oxoproline. To prepare the diastereomer mixture of the target compound it suffices to use step (A), employing as amino acid for the esterification D or L-5-oxoproline or one of its reactive derivatives of the general formula III without protective group ($R^5 = H$). Subsequently steps (B) and/or (D) are carried out to isolate the individual diastereomers Ia and Ib.

The individual process steps (A) to (H) will be further explained as far as necessary below.

Step A:

The amino acid derivatives of the general formula III protected at the amine nitrogen atom are esterified with the threo-4-alkoxy-5-arylhydroxymethyl-2(5H)-furanones of the general formula II, preferably in the presence of an aliphatic carbodiimide such as N,N'-dicyclohexylcarbodiimide as condensing agent and preferably in the presence of a 4-dialkylaminopyridine such as 4-dimethylamino or 4-pyrrolidinopyridine as acylation catalyst, preferably in an anhydrous aprotic solvent, for example a low halogen hydrocarbon such as chloroform or dichloromethane or a low aliphatic dialkyl ether or cyclic ether, or acetonitrile or dimethyl formamide at temperatures between $-30°$ and $+30°$ C., preferably between $-10°$ and $+10°$ C.

This procedure is particularly suitable for racemization-free esterification of chiral D or L-amino acids or their derivatives of the general formula III. However, other condensing agents known from peptide chemistry may also be used, in particular when achiral amino acids or their derivatives of the general formula III are employed for the esterification. The threo-4-alkoxy-5-arylhydroxymethyl-2(5H)-furanones of the general formula II used are usually employed as racemates.

Particularly preferred compounds of the general formula II are: threo-5-(2-fluorophenylhydroxymethyl)-, threo-5-(2-chlorophenylhydroxymethyl)-, threo-5-(2-bromophenylhydroxymethyl)-, threo-5-(2-trifluoromethylphenylhydroxymethyl)-, threo-5-(2-methylphenylhydroxymethyl)-, threo-5-(2,4-dichlorophenylhydroxymethyl)- and threo-5-(2,5-dichlorophenylhydroxymethyl)-4-methoxy-2(5H)-furanone.

As amino acids for the esterification in step (A) preferably alanine, phenylalanine, phenylglycine, proline, 5-oxoproline, glutamic acid, glutamine, methionine, glycine, 2-methylalanine, 1-amino-1-cyclohexane carboxylic acid and 4-aminobutyric acid or their reactive derivatives of the general formula III are used. As already mentioned, 5-oxoproline may also be used without the protective group $R^5$. If the radical $R^5$ is a low alkanoyl radical having 2 to 5 C atoms it is not a "protective group" but an acyl radical which cannot be split off acidically or hydrogenolytically.

Among the group of the chiral amino acids the respective L-forms are particularly preferred.

As other protective groups for amino groups of amino acids which are usual in peptide chemistry and can be acidically or hydrogenolytically split off it is possible to use for example 3,5-dimethoxyphenylisopropyloxycarbonyl (Ddz), 2-(4-biphenyl)-isopropyloxycarbonyl (Bpoc), 2-furylmethyloxycarbonyl (Foc), p-bromobenzyloxycarbonyl [Z(Br)] or p-methoxybenzyloxycarbonyl [Z (OMe)].

Amino acid derivatives of the general formula III protected in this manner are either known or can be made by methods given in the literature (cf. O. Keller et al., Org. Syntheses 63, 160 (1985); W. J. Paleveda et al., Org. Syntheses 63, 171 (1985); W. Grassmann and E. Wünsch, Chem. Ber. 91, 462 (1958); E. Wünsch in "Methoden der organischen Chemie", Vol. XV/1, Georg Thieme Verlag, Stuttgart 1974. Preferred protective groups are BOC and Z.

Step (B):

If in step (A) a chiral D or L-amino acid is used for esterification of the racemic threo-5-arylhydroxymethyl-4-alkoxy-2(5H)-furanones a mixture of the diastereomeric esters VIIa and VIIb is obtained. These can be separated by fractionated crystallization from solvents or solvent mixtures. Suitable solvents are low alcohols having 1 to 5 C atoms, for example methanol, ethanol, isopropanol, butanol, low aliphatic or cycloaliphatic ethers, for example diethylether, tert. butylmethylether and tetrahydrofurane, low aliphatic ketones, e.g. acetone or butanone, or low aliphatic carboxylic acid esters, in each case on their own or in mixtures with each other or in mixtures with hydrocarbons having 5 to 10 C atoms, for example pentane, hexane, heptane and cyclohexane.

For the separation the mixture is dissolved in one of the aforementioned solvents at elevated temperature, cooled, allowed to stand at temperatures between $-20°$ and $+30°$ C. and the sparsely soluble diastereomer precipitating first separated by filtration or centrifugation. It is also possible to carry out the dissolving at low temperatures or room temperature and before allowing to stand to concentrate the solution by evaporating a part of the solvent to achieve crystallization of the sparsely soluble diastereomer. The filtrate remaining after separation of the crystallizate is further concentrated, allowed to stand and again filtered to ensure as quantitative as possible a separation of the sparsley soluble diastereomer. The more readily soluble diastereomer is recovered or greatly concentrated by evaporation of the mother liquors and recrystallization from a second solvent or solvent mixture.

For example, ethanol is first used as solvent for separating the first diastereomer and the other diastereomer remaining in the mother liquors is purified by recrystallization from isopropanol or butanol possibly with admixture of for example pentane, hexane or tert. butylmethylether.

The aforementioned purification operations can be repeated as often as desired depending upon the required diastereomer purity. The purity can be checked in known manner by NMR spectroscopy, thin-layer chromatography, high-pressure liquid chromatography, polarimetry or by comparable usual methods.

Instead of by fractional crystallization the diastereomer separation may also be effected with the aid of chromatographic methods in a manner known per se, for example by column chromatography with for example chloroform/methanol or toluene/acetone as eluent on silica.

Step (C):

The splitting off of the protective group $R^5$ from the compounds of the general formulae I, VIIa or VIIb can be carried out either acidolytically or, in the case of protective groups belonging to the arylmethyloxycarbonyl series, by hydrogenolysis in the presence of a catalyst.

Acids suitable for the acidolysis are hydrochloric acid, hydrobromic acid or hydroiodic acid, acetic acid, trifluoroacetic acid and formic acid. The nature and concentration of the respective acid is chosen so that a selective splitting off of the protective group occurs without the ester bond being jeopardised. Usually, the splitting is carried out in a solvent. Suitable solvents are low alkane carboxylic acid esters, for example ethyl acetate, propyl acetate, ethyl propionate or the like, and the ethers described under step (B).

After mixing with the amount of acid necessary for the splitting the solutions of the compounds I, VIIa or VIIb in the respective solvent are allowed to stand at temperatures between $-20°$ and $+40°$ C. until the acidolysis is completely finished and the compounds are isolated in the form of the corresponding acid addition salts. Particularly preferred are solutions in ethyl acetate to which about 1 to 4 times the molar amount with respect to the ester of the general formula I with $R^5 \neq H$ of a solution of hydrogen bromide or hydrogen chloride in glacial acetic acid is added. The desired compounds of the general formulae VIII, VIIIa or VIIIb are obtained in the form of readily crystallizing hydrochlorides or hydrobromides which can be purified if desired by recrystallization from a low alcohol, ether, ester or mixtures thereof, possibly with addition of a hydrocarbon as solvent.

Alternatively, the splitting off of the protective group $R^5$ is effected by hydrogenolysis of the compounds of the general formulae I with $R^5 \neq H$, VIIa or VIIb in which $R^5$ denotes for example Z, Z(Br), Z(OMe), Ddz, Bpoc or Foc, in a manner known per se, preferably using a palladium catalyst, in a suitable solvent such as ethyl acetate, dioxane, ethanol or isopropanol. The compounds of the general formulae VIII, VIIIa or VIIIb are isolated in the form of their free bases and if desired converted to an acid addition salt, for example to the corresponding hydrochloride, hydrobromide, sulfate, hydrogen sulfate, methane sulfonate, fumarate, maleate, benzoate, citrate or the like.

Step (D):

If the esters of chiral D or L-amino acids were not separated into the diastereomers in step (B) or the separation was incomplete, the free amino acid esters of the formulae VIIIa and VIIIb, suitably in the form of their aforementioned acid addition salts, are separated into the diastereomers. The separation is carried out analogously to step (B) by fractional crystallization or chromatographically. Particularly suitable crystallization media are low alcohols, for example methanol, ethanol, propanol, isopropanol or butanol, aliphatic or cyclic ethers, low ketones, the compounds VIIIa or VIIIb also possibly occurring in the form of the azomethines or enamines formed with the ketones, and low alkane carboxylic acid esters, possibly with addition of hydrocarbons having 5 to 10 C atoms.

Step (E):

To prepare esters of the general formulae Ia or Ib in which the amino acid radical is achiral, i.e. esters of glycine, β-alanine, 2-methylalanine, 4-aminobutyric acid or 1-amino-1-cycloalkane carboxylic acids, as starting products the enantiomeric pure threo-5-arylhydroxymethyl-4-alkoxy-2-(5H)-furanones of the general formulae IIa or IIb are required. These are obtained by splitting of the esters of the general formulae VIIIa or VIIIb using an acid or alkali catalyst. Preferred esters here are esters of the D or L-proline and the D or L-phenylglycine which permit a particularly effective separation of the diastereomers VIIa and VIIb in step (B) of the process or the diastereomers VIIIa and VIIIb in step (D) of the process.

The splitting of the esters VIIIa and VIIIb may be catalyzed by an acid or a base. Preferably, the following conditions are observed:

Acidic splitting:

The compounds of the general formulae VIIIa and VIIIb are heated to temperatures between 50° and 120° C., preferably between 70° and 110° C., in aqueous solution or suspension, possibly in a mixture with low alcohols, with addition of at least equivalent amounts of hydrochloric or hydrobromic acid, sulfuric or phosphoric acid, a sulfonic acid, for example methane or p-toluene sulfonic acid, or a strong organic acid such as oxalic acid, until the splitting is complete.

Alkali-catalyzed splitting (transesterification):

Solutions or suspensions of the compounds VIIIa and VIIIb in a low anhydrous alcohol, preferably methanol or ethanol, are mixed with an anhydrous alkali carbonate, preferably lithium carbonate, and stirred at temperatures between −20° and +40° C., preferrably between 0° and 20° C., until the splitting is complete.

Step (F):

The enantiomers obtained in step (E) and of the formulae IIa or IIb are reacted analogously to step (A) with the amino acid derivatives, substituted at the amino group by the radical $R^5$, of the general formula III of glycine, β-alanine, 2-methylalanine, 4-aminobutyric acid or 1-amino-1-cycloalkane carboxylic acids to give compounds of the general formulae VIIa and VIIb respectively, VIIa and VIIb being optical antipodes.

Step (G):

If desired, the compounds VIIa and VIIb obtained in step (F) can be split analogously to step (C) to give the free amino acid esters of the formulae VIIIa and VIIIb, which also represent optical antipodes. The reaction conditions are analogous. The compounds of the general formulae VIIIa and VIIIb are also preferably isolated in the form of their acid addition salts.

Step (H):

It is preferred in some cases for the preparation of the compounds of the general formulae I, Ia or Ib, wherein $R^1$, $R^2$, $R^3$, $R^4$, $R^5$ and A have the meanings described in conjunction with the explanation of general formula I, with the provision that $R^5$ only denotes low alkanoyl having 2 to 5 C atoms, firstly to synthesize the compounds of the general formulae VIIa and/or VIIb in which $R^5$ has another meaning than low alkanoyl, for example is BOC, Z, Foc or Bpoc. The desired compounds of the formulae I, Ia or Ib can then be obtained therefrom, after having split off the protective group analogously to step (C) or (G), by acylation of the then present compounds of the general formulae VIII, VIIIa or VIIIb with a reactive low alkanoyl derivative of the general formulae $R^5$—Y or $R^5$—O—$R^5$, wherein $R^5$ is a low alkanoyl having 2 to 5 C atoms, preferably acetyl, and Y is a chlorine or bromine atom.

The acylation is carried out in an aprotic solvent, preferably a low halogen hydrocarbon, for example dichloromethane or chloroform, or in an aliphatic or cycloaliphatic ether in the presence of an auxiliary base, preferably pyridine or triethylamine, possibly in the presence of an acylation catalyst, preferably 4-dimethylamino or 4-pyrrolidinopyridine at temperatures between −30° and +50° C., preferably between 0° and 30° C. However, other acylation methods with which the expert is familiar may also be used, for example acylation with a ketene of the formula $R^7$=C=O wherein $R^7$ is an alkylidene group having 1 to 4 C atoms.

As already mentioned, the subject of the invention further includes pharmaceutical compositions which possibly together with a pharmaceutically inert excipient contain one or more of the compounds of the general formula I. These drugs and pharmaceutical preparations may be used as anticonvulsives in human and veterinary medicine and as antiepileptics in human medicine. The effective dose in which the compounds can be administered lies both in human medicine and in veterinary medicine between about 0.05 and 10 mg/kg. 5 to 500 mg of the active substance may be administered once or several times daily. As pharmacologically inert usual carrier and auxiliary substances it is possible to employ for example water, vegetable oils, polyethylene glycols, glycerine esters, gelatines, carbohydrates such as lactose or starch, magnesium stearate, talc, vaselines, preservatives, stabilizers, lubricants, wetting agents, emulsifiers, physiologically harmless salts, buffer substances, dyes, flavouring substances and aroma. The selection of the pharmacologically inert excipient depends on whether the active substances are to be administered enterally, parenterally or topically. The compounds can also be administered mixed with other active substances, for example vitamines or other known anticonvulsives or antiepileptics.

Each of the compounds according to the invention specified in the following examples represents an agent particularly suitable for making pharmaceutical preparations.

The following should be noted with regard to the examples:

Temperatures are given in ° C. and uncorrected. Pressures are given in mbar, 1 mbar $\triangleq 10^2$ Pa. Optical rotations are given as specific rotations [α], measured at the wavelength λ=489 nm of the D-line of the sodium spectrum and, unless otherwise stated, at 20° C. In brackets the concentration c[g/100 ml] and the solvent used are indicated. The $^1H$ and $^{13}C$ nuclear magnetic resonance spectra were taken in DMSO-$D_6$, unless otherwise stated. The chemical shifts are given in ppm relatively to the tetramethylsilane signal (internal standard). Coupling constants J are in Hertz (Hz). The following abbreviations are used to denote the multiplicities: s=singlet, d=doublet, t=triplet, q=quartet, m=multiplet, br.=broad or broadened. Furthermore, the following abbreviations are used: b.p.=boiling point, m.p.=melting point.

In the separation of diastereomers the L-amino acid esters of the optical dextrorotary threo-5-arylhydroxymethyl-2(5H)-furanones and the D-amino acid esters of the corresponding laevorotary -2(5H)-furanones are denoted diastereomers A whilst the L-amino acid esters of laevorotary -2(5H)-furanones and the D-amino acid esters of the corresponding dextrorotary -2(5H)-furanones are denoted diastereomers B.

The thin-layer chromatographic (TLC) determination of Rf values was on silica (TLC ready-for-use plates) with 10 cm running height of the eluent. The substance stains were rendered visible by fluorescence extinction at 254 nm, colouring with iodine vapour or with ninhydrin spray reagent.

The racemic threo-4-alkoxy-5-arylhydroxymethyl-2(5H)-furanones of the general formula II required as starting material may be prepared for example by the process known from German patent application P 36 15 157.2 or in analogous manner. The entire content of said German patent application is incorporated into the present description by this reference thereto.

The following examples numbers 1 to 101 are reference examples for the preparation of the starting products of the general formula II. The compounds according to the examples numbers 30 to 32, 36, 62, 63, 90 and 91 are novel. Examples numbers 102 to 141 and 150 to 157 relate to amino acid esters according to the invention. Examples numbers 142 to 149 relate to optically active threo-5-arylhydroxymethyl-4-methoxy-2(5H)-furanones of the general formulae IIa and IIb which can be used as reactive intermediate products for the preparation of the amino acid esters according to the invention.

EXAMPLE 1

Ethyl-3-methoxy-2(E)-butenoate

The mixture of 520 g (4 mole) ethyl acetoacetate, 400 ml methanol and 2 ml 36% hydrochloric acid(or 1 ml conc. sulfuric acid) is heated to 50° C. Whilst stirring 425 g (4 mole) trimethyl orthoformate are added dropwise such that the mixture is kept at about 50° C. Thereafter the methyl formate formed and excess methanol are distilled off and the residue fractionated over a Vigreux column. 548 g (3.8 mole) pure ethyl-3-methoxy-2(E)-butenoate distill over between 184° C. and 186° C. Yield: 95%.

EXAMPLE 2

Ethyl-3-ethoxy-2(E)-butenoate

Preparation analogous to example 1 by reacting ethyl acetoacetate with triethyl orthoformate in ethanol with hydrochloric acid as catalyst.
Yield: 84.5%
B.p.=191°–195° C. M.p.=31°–33° C.

EXAMPLE 3

Methyl-3-methoxy-2(E)-pentenoate

Preparation analogous to example 1 by reacting methyl-3-oxopentanoate with trimethyl orthoformate in methanol and sulfuric acid as catalyst. Yield: 87.7%. B.p.=76°–78° C. (20 mbar).

EXAMPLE 4

3-methoxy-5-phenyl-2(E),4(E)-pentadienoic acid:

Method a:

To the mixture of 53 g (0.5 mole) benzaldehyde 100 ml dimethyl sulfoxide and 72 g (0.5 mole) ethyl-3-methoxy-2(E)-butenoate whilst stirring and under a nitrogen atmosphere 11.6 g (0.05 mole) benzyltriethyl ammonium chloride is added and thereafter the solution of 33.6 g (0.6 mole) potassium hydroxide in 35 ml water added dropwise. Heating is carried out for 16 hours to 110° C., the solution evaporated, the residue dissolved in 400 ml water and the starting products and by-products extracted with 100 ml dichloroethane. The crude product precipitates out of the aqueous phase after acidifying with 70 ml 10M hydrochloric acid and after filtering off by suction, washing acid free with water, recrystallization from ethanol and drying at 100° C. in vacuum gives 34.9 g (0.171 mole) pure product with m.p.=154°–155° C. Yield: 34.2%.

Literature m.p.=157.5°–158° C [E. E. Smissman and A. N. Voleng, J Org. Chem. 29, 3161 (1964)].

Analysis: $C_{12}H_{12}O_3$ (204.23) Calc.: C (70.57), H (5.92) Found: C (70.49), H (6.16)

Method b:

To the solution of 3785 g (26.25 mole) ethyl-3-methoxy-2(E)-butenoate in 6 liters dimethyl sulfoxide whilst stirring and under a nitrogen atmosphere 2653 g (25 mole) benzaldehyde and 926 ml (2.5 mole) 40% aqueous tetraethyl ammonium hydroxide are consecutively added dropwise. After heating to 100° C. the solution of 1470 g (26.25 mole) potassium hydroxide in 1500 ml water is added dropwise and stirring continued for 4 hours at 100° C. After cooling to about 20° C. the mixture is poured into about 50 liters of water and impurities extracted with 10 liters dichloromethane. The aqueous phase is acidified with vigorous stirring with about 3 liters 33% hydrochloric acid to pH=2 and the precipitated crude product filtered off via a pressure filter, washed free of chloride with water and blown dry with nitrogen. The filter cake is suspended in 6 liters ethanol, again filtered and after blow drying dried in a vacuum up to the end temperature of 85° C. 3071 g (15.04 mole) pure product is obtained with m.p. 159°–160° C. Yield: 60.1%.

EXAMPLE 5

5-(2-chlorophenyl)-3-methoxy-2(E),4(E)-pentadienoic acid 3785 g (26.25 mole) ethyl-3-methoxy-2(E)-butenoate are reacted analogously to example 4 b in 6 liters dimethyl sulfoxide with 3515 g (25 mole) 2-chlorobenzaldehyde, 926 ml (2.5 mole) 40% tetraethyl ammonium hydroxide and 2940 g (26.25 mole) 50% aqueous KOH-solution and then stirred for 4 hours at 100° C. After cooling dilution is carried out with 10 liters of water and byproducts extracted with 10 liters dichloromethane. The aqueous phase is stirred into the mixture of 3 liters 33% hydrochloric acid and 50 liters water, whereafter the pH value is 3.5 to 4. After filtering, washing with water until free of chloride and blow drying, the precipitated crude product is suspended in 20 liters ethanol, again suction filtered, blow dried and dried up to the end temperature of 85° C. at 20 mbar. 5045 g (21.14 mole) pure product is obtained with m.p. 202° C. Yield: 84.55%.

Analysis: $C_{12}H_{11}ClO_3$ (238.67) Calc.: C (60.39) H (4.65), Cl (14.85) Found: C (60.33) H (4.85), Cl (14.72)

300 MHz-$^1$H-NMR: 11.8–12.2(1 H, br.m, COOH), 8.08 (1 H, d, $J_{5/4}$=16 Hz, H-5), 7.54 (1 H, d, $J_{4/5}$=16 Hz, H-4), 5.29 (1 H, s, H-2), 3.785 (3 H, s, OCH$_3$), 7.35–7.75 (4 H, m, aromat. protons ).

Analogously to the synthesis methods used in examples 4 a, b and 5, by condensation of benzaldehyde or substituted benzaldehydes with the 3-alkoxy-2(E)-alkenoates described in examples 1 to 3 the following 3-alkoxy-5(subst.)phenyl-2(E),4(E)-pentadienoic acids are prepared: see Table 1.

TABLE 1

| | 3-Alkoxy-5-phenylpentadienoic acids | | |
|---|---|---|---|
| Example No. | designation | yield [%]* | m.p. [°C.] (recrystallised from) |
| 6 | 5-(2-chlorophenyl)-3-ethoxy-2(E),4(E)-pentadienoic acid | 41 | 179–181 (ethanol) |
| 7 | 5-(2-chlorophenyl)-3-methoxy-4-methyl-2(E),4(E)-pentadienoic acid | 24 | 126–128 (methanal) |
| 8 | 5-(4-chlorophenyl)-3-methoxy-2(E),4(E)-pentadienoic acid | 36 | 200 (ethanol) |
| 9 | 5-(2-bromophenyl)-3-methoxy-2(E),4(E)-pentadienoic acid | 71 | 206–207 (ethanol) |
| 10 | 5-(3-bromophenyl)-3-methoxy-2(E),4(E)-pentadienoic acid | 14 | 161–163 (ethanol) |
| 11 | 5-(2-fluorophenyl)-3-methoxy 2(E),4(E)-pentadienoic acid | 66 | 188–190 (ethanol) |
| 12 | 5-(2-trifluoromethylphenyl)-3-methoxy-2(E),4(E)-pentadienoic acid | 15 | 173–174 (ether) |

TABLE 1-continued

3-Alkoxy-5-phenylpentadienoic acids

| Example No. | designation | yield [%]* | m.p. [°C.] (recrystallised from) |
|---|---|---|---|
| 13 | 5-(3-trifluoromethylphenyl)-3-methoxy-2(E),4(E)-pentadienoic acid | 41 | 152–153 (ethanol) |
| 14 | 5-(4-trifluoromethylphenyl)-3-methoxy-2(E),4(E)-pentadienoic acid | 32 | 181–183 (methanol) |
| 15 | 3-methoxy-5-(2-nitrophenyl)-2(E),4(E)-pentadienoic acid | | 209–211 (ethanol) |
| 16 | 3-methoxy-5-(3-nitrophenyl)-2(E),4(E)-pentadienoic acid | 9 | 198–199 |
| 17 | 3-methoxy-5-(2,5-dimethylphenyl)-2(E),4(E)-pentadienoic acid | 49 | 161–162 (ether) |
| 18 | 5-(2-chloro-5-methylphenyl)-3-methoxy-2(E),4(E)-pentadienoic acid | 48 | 179–181 (methanol) |
| 19 | 5-(2,3-dichlorophenyl)-3-methoxy-2(E),4(E)-pentadienoic acid | 10 | 215–216 (ethanol) |
| 20 | 5-(2,4-dichlorophenyl)-3-methoxy-2(E),4(E)-pentadienoic acid | 73 | 196–197 (ethanol) |
| 21 | 5-(2,4-dichlorophenyl)-3-ethoxy-2(E),4(E)-pentadienoic acid | 50 | 198–200 (ethanol) |
| 22 | 5-(2,5-dichlorophenyl)-3-methoxy-2(E),4(E)-pentadienoic acid | 55 | 198–199 (ethanol) |
| 23 | 5-(2,5-dichlorophenyl)-3-ethoxy-2(E),4(E)-pentadienoic acid | 49 | 213–215 (ethanol) |
| 24 | 5-(3,4-dichlorophenyl)-3-methoxy-2(E),4(E)-pentadienoic acid | 46 | 188–190 (ethanol) |
| 25 | 5-(3,5-dichlorophenyl)-3-methoxy 2(E),4(E)-pentadienoic acid | 38 | 211–213 (2-propanol) |
| 26 | 5-[3,5-bis-(trifluoromethyl)-phenyl]-3-methoxy-2(E),4(E)-pentadienoic acid | 6 | 217–219 (chloroform) |
| 27 | 5-(2-chloro-5-trifluoromethylphenyl)-3-methoxy-2(E),4(E)-pentadienoic acid | 40 | 188–192 (ethanol) |
| 28 | 5-(4-chloro-2-trifluoromethylphenyl)-3-methoxy-2(E),4(E)-pentadienoic acid | 22 | 190–193 (ethanol) |
| 29 | 5-(4-bromo-2-chlorophenyl)-3-methoxy-2(E),4(E)-pentadienoic acid | 66 | 192–194 (acetone) |
| 30 | 3-methoxy-5-(2,6-dimethylphenyl)-2(E),4(E)-pentadienoic acid | 20 | 168–170 (ethanol/water) |
| 31 | 3-methoxy-5-(2-methylphenyl)-2(E),4(E)-pentadienoic acid | 70 | 174–176 (ethanol) |
| 32 | 5-(2,4-difluorophenyl)-3-methoxy-2(E),4(E)-pentadienoic acid | 27 | 180–182 (ethanol/water) |

*In the case of yields below 50%, reaction, working up and recrystallisation conditions not yet optimised.

EXAMPLE 33

Benzyl-5-(2-chlorophenyl)-3-methoxy-2(E),4(E)-pentadienoate

Whilst stirring, 34.2 g (0.2 mole) benzyl bromide is added dropwise to the mixture of 48 g (0.2 mole) 5-(2-chlorophenyl)-3-methoxy-2(E), 4(E)-pentadienoic acid, 600 ml acetone and 60 g (0.43 mole) potassium carbonate and heated under reflux for 16 hours. After filtering off inorganic residues, evaporation of the filtrate and recrystallization from tert. butylmethyl ether, 56.1 g (0.17 mole) pure benzyl ester with m.p. 83–86° C. is obtained. Yield: 85%

Analysis: $C_{19}H_{17}ClO_3$ (328.80) Calc.: C (69.41), H (5.21), Cl(10.78) Found: C (69.42), H (5.08), Cl(100.9).

EXAMPLE 34

Ethyl-5-(2-chlorophenyl)-3-methoxy-2(E),4(E)-pentadienoate (a) The mixture of 31 g (0.13 mole) 5-(2-chlorophenyl)-3-methoxy-2(E),4(E)-pentadienoic acid, 400 ml acetone, 36 g (0.26 mole) potassium carbonate and 20.8 g (0.13 mole) ethyl iodide is heated to boil under reflux for 18 hours. After cooling, filtering and evaporating the filtrate the oily crude product is taken up in 100 ml n-pentane, insoluble potassium iodide filtered off, the filtrate evaporated and dried at 45° C. and 20 mbar. 33.3 g (0.125 mole) pure ethyl ester with m.p. 49°–51° C. is obtained. Yield: 96%.

Analysis: $C_{14}H_{15}ClO_3$ (266.73) Calc.: C (63.05), H (5.67), Cl (13.29) Found: C (63.37), H (5.69), Cl (13.3)

(b) To the mixture of 35 liters butanone, 2386 g (10 mole) 5-(2-chlorophenyl)-3-methoxy-2(E),4(E)-pentadienoic acid, 2073 g (15 mole) potassium carbonate and 16.6 g (0.1 mole) potassium iodide, whilst stirring at 56° C. 1635 g (15 mole) ethyl bromide is added and stirring carried out for 24 hours at 56° C. After cooling and filtering off inorganic components the filtrate is washed twice with 10 liters water and the butanone phase evaporated. 2348 g (8.80 mole) ethyl ester is obtained which crystallizes on cooling. TLC-chromatography and infra-red spectrum show the identity with the previously described product (34 a). M.p. 45° C. Yield: 88%.

EXAMPLE 35

Methyl-5-(2-chlorophenyl)-3-methoxy-2(E),4(E)-pentadienoate

The mixture of 23.9 g (0.1 mole) 5-(2-chlorophenyl)-3- methoxy-2(E),4(E)-pentadienoic acid, 500 ml acetone and 30.4 g (0.22 mole) potassium carbonate is mixed whilst stirring with 9.5 ml (0.1 mole) dimethyl sulfate and heated under reflux for 4 hours. After cooling and filtering the filtrate is evaporated, the crude product dissolved in 100 ml chloroform, washed twice with 30 ml water, the chloroform phase evaporated, and recrystallization carried out from isopropanol/water. After drying at 50° C./20 mbar, 22.18 g (87.8 mmole) pure methyl ester is obtained with m.p. 50°–52° C. Yield: 87.8%.

Analysis: $C_{13}H_{13}ClO_3$ (252.69) Calc.: C (61.79), H (5.18), Cl (14.03) Found: C (61.30), H (5.07), Cl (13.7)

Analogously to the methods described in examples 33 to 35 the 3-alkoxy-5-phenyl-2(E),4(E)-pentadienoic acid esters set forth in Table 2 were prepared.

TABLE 2

3-Alkoxy-5-phenylpentadienoates

| Example No. | designation | yield [%] | m.p. [°C.] (recrystallised from) |
|---|---|---|---|
| 36 | ethyl 3-methoxy-(2-methylphenyl)-2(E),4(E)-penta- | 90 | oil (evaporated) |

TABLE 2-continued

3-Alkoxy-5-phenylpentadienoates

| Example No. | designation | yield [%] | m.p. [°C.] (recrystallised from) |
|---|---|---|---|
| | dienoate | | |
| 37 | isopropyl 5-(2-chlorophenyl)-3-methoxy-2(E),4(E)-pentadienoate | 95 | 55–58 (pentane) |
| 38 | sec.-butyl 5-(2-chlorophenyl)-3-methoxy-2(E),4(E)-pentadienoate | 85 | 41–42 (isopropanol/water) |
| 39 | tert.-butyl 5-(2-chlorophenyl)-3-methoxy-2(E),4(E)-pentadienoate | 30 | oil (evaporated) |
| 40 | ethyl 3-methoxy-5-phenyl-2(E),4(E)-pentadienoate | 96 | 34 (evaporated) |
| 41 | ethyl 5-(2-chlorophenyl)-3-ethoxy-2(E),4(E)-pentadienoate | 85 | 79–81 (methanol) |
| 42 | ethyl 5-(4-chlorophenyl)-3-methoxy-2(E),4(E)-pentadienoate | 94 | 52–53 (isopropanol/pentane) |
| 43 | ethyl 5-(2-bromophenyl)-3-methoxy-2(E),4(E)-pentadienoate | 98 | 45–46 (pentane) |
| 44 | ethyl 5-(2-fluorophenyl)-3-methoxy-2(E),4(E)-pentadienoate | 99 | 46–48 (isopropanol) |
| 45 | ethyl 5-(2-trifluoromethylphenyl)-3-methoxy-2(E),4(E)-pentadienoate | 99 | 75 (ethanol) |
| 46 | ethyl 5-(3-trifluoromethylphenyl)-3-methoxy-2(E),4(E)-pentadienoate | 92 | 46–47 (ethanol) |
| 47 | ethyl 5-(4-trifluoromethylphenyl)-3-methoxy-2(E),4(E)-pentadienoate | 52 | 42–44 (ethanol) |
| 48 | ethyl 3-methoxy-5-(2,5-dimethylphenyl)-2(E),4(E)-pentadienoate | 94 | 53–54 (ethanol) |
| 49 | ethyl 5-(2-chloro-5-methylphenyl)-3-methoxy-2(E),4(E)-pentadienoate | 95 | 76–78 (ethanol) |
| 50 | ethyl 5-(2,3-dichlorophenyl)-3-methoxy-2(E),4(E)-pentadienoate | 78 | 110–111 (ethanol) |
| 51 | ethyl 5-(2,4-dichlorophenyl)-3-methoxy-2(E),4(E)-pentadienoate | 92 | 81–83 (isopropanol) |
| 52 | ethyl 5-(2,4-dichlorophenyl)-3-ethoxy-2(E),4(E)-pentadienoate | 92 | 64–67 (isopropanol) |
| 53 | ethyl 5-(2,5-dichlorophenyl)-3-methoxy-2(E),4(E)-pentadienoate | 92 | 97–98 (ethanol) |
| 54 | ethyl 5-(2,5-dichlorophenyl)-3-ethoxy-2(E),4(E)-pentadienoate | 64 | 87–90 (isopropanol) |
| 55 | ethyl 5-(3,4-dichlorophenyl)-3-methoxy-2(E),4(E)-pentadienoate | 89 | 76–78 (ethanol) |
| 56 | ethyl 5-(3,5-dichlorophenyl)-3-methoxy-2(E),4(E)-pentadienoate | 93 | 89–91 (ethanol) |
| 57 | ethyl 5-[3,5-bis-(trifluoromethyl)-phenyl]-3-methoxy-2(E),4(E)-pentadienoate | 88 | 86–88 (evaporated) |
| 58 | ethyl 5-(2-chloro-5-trifluoromethylphenyl)-3-methoxy-2(E),4(E)-pentadienoate | 76 | 47–50 (ethanol) |
| 59 | ethyl 5-(4-chloro-2-trifluoromethylphenyl)-3-methoxy-2(E),4(E)-pentadienoate | 92 | 79–80 (ethanol/water) |
| 60 | ethyl 5-(4-bromo-2-chlorophenyl-3-methoxy-2(E),4(E)-pentadienoate | 91 | 91–93 (ethanol) |
| 61 | ethyl 5-(2-chlorophenyl)-3-methoxy-4-methyl-2(E),4(E)-pentadienoate | 98 | oil (evaporated) |
| 62 | ethyl 5-(2,6-dimethylphenyl)-3-methoxy-2(E),4(E)-pentadienoate | 91 | 101–103 (ethanol) |
| 63 | ethyl 5-(2,4-difluorophenyl)- | 98 | 67–68 |

TABLE 2-continued

| | 3-Alkoxy-5-phenylpentadienoates | | |
|---|---|---|---|
| Example No. | designation | yield [%] | m.p. [°C.] (recrystallised from) |
| | 3-methoxy-2(E),4(E)-pentadienoate | | |

EXAMPLE 64 threo-5-(2-chlorophenylhydroxymethyl)-4-methoxy-2(5H)-furanone

With the aid of the synthesis of this starting compound the various embodiments are given of the oxidation, catalyzed by osmium tetroxide, of the 3-alkoxy-5-phenyl-2(E),4(E)-pentadienoic acid derivatives to give the threo-4-alkoxy-5-phenylhydroxymethyl-2(5H)-furanones.

Process variant a:

To a mixture of 48.0 g (201 mmole) 5-(2-chlorophenyl)-3-methoxy-2(E),4(E)-pentadienoic acid, 400 ml water and 400 ml (566 mmole) 20% aqueous tetraethylammonium hydroxide is added, with stirring and cooling to 0° C., 50 ml of a 0.02M solution of osmium tetroxide in acetone or tert. butanol and 56 ml (403 mmole) 70% aqueous tert. butyl hydroperoxide. After stirring for 6 hours at 0° C., the reaction mixture is left to stand for 8 days at 0°–5° C. and thereafter excess hydroperoxide is reduced by stirring with 10% aqueous sodium sulfite solution. By the addition of 1M sulfuric acid the pH is adjusted to 2, unreacted starting product thereby crystallizing out. This is filtered off with suction (10.1 g $\hat{=}$ 42 3 mmole). The filtrate is extracted three times with 100 ml chloroform and the extract is washed free of quaternary ammonium salts with 50 ml 1M hydrochloric acid. The extract contains a mixture of threo-5-(2-chlorophenyl)-4,5-dihydroxy-3-methoxy-2(E)-pentenoic acid and threo-5-(2-chlorophenylhydroxymethyl)-4-methoxy-2(5H)-furanone. By evaporation, the ring closure is completed to give, after recrystallization from ethyl acetate, 18.12 g (71.2 mmole) of pure threo-5-(2-chlorophenylhydroxymethyl)-4-methoxy-2(5H)-furanone; m.p. 149°–151° C. Yield based on reacted starting material: 45.1%.

Analysis: $c_{12}H_{11}ClO_4$ (254.67) calc.: C (56.59), H (4.35), Cl (13.92) found: C (56.27), H (4.35), Cl (14.0)

300 MHz—$^1$—NMR: 7.3–7.7 (4H, m, aromatic protons), 5.96 (1H, d, $J_{OH/H\alpha}$=5.5 Hz, α-OH), 5.440 (1 H, d, $J_{H-3/H-5}$=1.3 Hz, H-3), 5.225 (1 H, dd, $J_{H\alpha/H-5}$=2 Hz, Hα), 5.008 (1 H, s, H-5) 3.923 (3 H, s, OCH$_3$)

75.46 MHz-$^{13}$C-NMR (broad band decoupled): C-2 (172.530), C-3 (90.268), C-4 (180.229) C-5 (79.872), C-α(66.721), $C_{Ar}$-1' (138.409), $C_{Ar}$-2' to 6' (130.650, 129.571, 129.421, 129.032 and 127.265), OCH$_3$ (60.071).

The assignment of the $^{13}$C-signals was verified by off-resonance and gated spectrum, as well as by SFORD experiments.

Process variant b:

To a solution of 26.7 g (100 mmole) ethyl 5-(2-chlorophenyl)-3-methoxy-2(E),4(E)-pentadienoate in 450 ml acetone are added 6.5 g (25 mmole) tetraethylammonium acetate tetrahydrate and successively there is added dropwise thereto, with stirring and cooling to 0° C., 25 ml 0.02M osmium tetroxide solution in tert. butanol and 23.6 ml (170 mmole) 70% aqueous tert. butyl hydroperoxide. The reaction mixture is left to stand for 12 days at 4° C., 200 ml dichloromethane and 140 ml 10% aqueous sodium sulfite solution are added thereto, stirred until no more hydroperoxide is detectable, the organic phase is separated off, the aqueous phase is extracted twice with 100 ml amounts of dichloromethane and the combined organic phases are washed with aqueous sodium chloride solution. The organic phase contains a mixture of threo-ethyl 5-(2-chlorophenyl)-4,5-dihydroxy-3-methoxy-2(E)-pentenoate and threo-5-(2-chlorophenylhydroxymethyl)-4-methoxy-2(5H)-furanone. By evaporation, the ring closure is completed to give, after recrystallization from tert. butyl methyl ether, 19.4 g (76.2 mmole) of pure product (m.p. 149°–151° C.) which is thin-layer chromatographically and IR-spectroscopically identical with the product obtained according to Example 64a. Yield: 72.6%.

Process variant c:

As in the case of variant b but, instead of the ethyl ester, there is used benzyl 5-(2-chlorophenyl)-3-methoxy-2(E),4(E)-pentadienoate. Yield of threo-5-(2-chlorophenylhydroxymethyl)-4-methoxy-2(5H)-furanone after recrystallization from ethanol: 67.5%. M.p. 149°–151° C.

Process variant d:

To a solution of 26.7 g (100 mmole) ethyl 5-(2-chlorophenyl)-3-methoxy-2(E),4(E)-pentadienoate in 360 ml. acetone are added, with stirring, 10 ml 0.02 molar osmium tetroxide solution in tert. butanol and a solution of 14.9 g (110 mmole) N-methylmorpholine N-oxide hydrate in 30 ml water and stirred for 4 days at ambient temperature. By stirring with 5.2 g (50 mmole) sodium bisulfite dissolved in 50 ml water, excess N-oxide is reduced and the pH is adjusted with 1M sulfuric acid to 4. Acetone is stripped off in a vacuum and the remaining aqueous mixture is extracted twice with 200 ml amounts of dichloromethane. The extract is washed free from N-methylmorpholine with dilute sulfuric acid and water and, after drying over anhydrous sodium sulfate, is concentrated in a vacuum. 18.13 g threo-5-(2-chlorophenylhydroxymethyl)-4-methoxy-2(5H)-furanone crystallize out. Evaporation of the filtrate and recrystallization from ethyl acetate gives a further 1.20 g of pure product.

Yield: 19.33 g (75.9 mmole) $\hat{=}$ 75.9%

Process variant e:

As in the case of variant d but the reaction is carried out, instead of in acetone, in two-phase system butanone/water and instead of 110 mmole there are used 160 mmole N-methylmorpholine N-oxide. Yield: 76.2%.

Process variant f:

As in the case of variant d but in two-phase system dichloromethane/water. Yield' 66.7%.

Process variant g:

The mixture of 23.6 g (80 mmole) sec. butyl 5-(2-chlorophenyl)-3-methoxy-2(E),4(E)-pentadienoate, 200 ml butanone, 15 ml 0.02M osmium tetroxide solution in tert. butanol, 17.6 g (160 mmole) N-methylmorpholine N-oxide hydrate and 50 ml water is stirred for 7 days at ambient temperature. After the addition of 100 ml dichloromethane, the reaction mixture is stirred with 100 ml 2% aqueous sodium bisulfite solution, the organic phase is separated off and washed twice with 100 ml amounts of 0.5 M hydrochloric acid and 5 times with 100 ml amounts of water. The organic phase contains a mixture of threo-sec. butyl 5-(2-chlorophenyl)-4,5-dihydroxy-3-methoxy-2(E)-pentenoate and threo-5-(2-chlorophenylhydroxymethyl)-4-methoxy-2(5H)-furanone. By the addition of 0.1 ml 32% hydrochloric acid and the evaporation of the organic phase, the ring closure is completed to give, after recrystallization from diethyl ether, 10.66 g (41.9 mmole) threo-5-(2-chlorophenylhydroxymethyl)-4-methoxy-2(5H)-furanone. Yield: 52.3%.

In the same way, instead of the sec. butyl ester, there can be used the corresponding methyl, isopropyl or tert. butyl esters.

Analogously to the process variants a to g described in Example 64, by the oxidation of the 3-alkoxy-5-phenyl-2(E), 4(E)-pentadienoic acid derivatives described in Examples 4 to 63, the following threo-4-alkoxy-5-phenylhydroxymethyl-2(5H)-furanone derivatives are prepared: cf. Table 3.

TABLE 3 threo-4-alkoxy-5-phenylhydroxymethyl-2(5H)-furanones

| Example No. | designation | Variant | yield [%] | m.p. [°C.] (recrystallised from) |
|---|---|---|---|---|
| 65 | threo-4-methoxy-5-phenylhydroxymethyl-2(5H)-furanone | a | 46 | 157 (dichloromethane) |
|  |  | b | 49 |  |
|  |  | d | 59 |  |
| 66 | threo-5-(2-chlorophenylhydroxymethyl)-4-ethoxy-2(5H-furanone | a | 24 | 114–116 (isopropanol) |
| 67 | threo-5-(4-chlorophenylhydroxymethyl)-4-methoxy-2(5H)-furanone | b | 47 | 148–150 (dichloromethane) |
| 68 | threo-5-(2-bromophenylhydroxymethyl)-4-methoxy-2(5H)-furanone | d | 85 | 162–164 (dichloromethane) |
| 69 | threo-5-(3-bromophenylhydroxymethyl)-4-methoxy-2(5H)-furanone |  | 50 | 167–168 (acetone/ethanol) |
| 70 | threo-5-(2-fluorophenylhydroxymethyl)-4-methoxy-2(5H)-furanone | d | 87 | 130–133 (dichloromethane) |
| 71 | threo-4-methoxy-5-(2-trifluoromethylphenylhydroxymethyl)-2(5H)-furanone | b | 62 | 166–167 (ethanol/water) |
| 72 | threo-4-methoxy-5-(3-trifluoromethylphenylhydroxymethyl)-2(5H)-furanone | b | 27 | 128–129 (ethanol/water) |
| 73 | threo-4-methoxy-5-(4-trifluoromethylphenylhydroxymethyl)-2(5H)-furanone | b | 28 | 171 (methanol) |
| 74 | threo-4-methoxy-5-(2-nitrophenylhydroxymethyl)-2(5H)-furanone | a | 10 | 170–172 (ethyl acetate) |
| 75 | threo-4-methoxy-5-(3-nitrophenylhydroxymethyl)-2(5H)-furanone | a | 21 | 149–151 (ethyl acetate) |
| 76 | threo-5-(2,5-dimethylphenylhydroxymethyl)-4-methoxy-2(5H)-furanone | b | 47 | 171–173 (ethanol) |
| 77 | threo-5-[(2-chloro-5-methylphenyl)-hydroxymethyl]-4-methoxy-2(5H)-furanone | b | 71 | 174–175 (methanol) |
| 78 | threo-5-(2,3-dichlorophenylhydroxymethyl)-4-methoxy-2(5H)-furanone | e | 75 | 161–162 (methanol) |
| 79 | threo-5-(2,4-dichlorophenylhydroxymethyl)-4-methoxy-2(5H)-furanone | a | 38 | 174 (dichloromethane) |
|  |  | b | 87 |  |
|  |  | e | 55 |  |
| 80 | threo-5-(2,4-dichlorophenylhydroxymethyl)-4-ethoxy-2(5H)-furanone | b | 72 | 133 (isopropanol) |
| 81 | threo-5-(2,5-dichlorophenylhydroxymethyl)-4-methoxy-2(5H)-furanone | a | 15 | 187 (dichloromethane) |
|  |  | b | 70 |  |
| 82 | threo-5-(2,5-dichlorophenylhydroxymethyl)-4-ethoxy-2(5H)-furanone | b | 70 | 175–178 (isopropanol) |
| 83 | threo-5-(3,4-dichlorophenylhydroxymethyl)-4-methoxy-2(5H)-furanone | b | 53 | 158–159 (ethyl acetate) |
| 84 | threo-5-(3,5-dichlorophenylhydroxymethyl)-4-methoxy-2(5H)-furanone | b | 62 | 177–179 (ethanol) |
| 85 | threo-5-[3,5-bis(trifluoromethyl)-phenylhydroxymethyl]-4-methoxy-2(5H)-furanone | e | 52 | 191–194 (ethyl acetate) |
| 86 | threo-5-[(2-chloro-5-trifluoromethylphenyl)-hydroxymethyl]-4-methoxy-2(5H)-furanone | e | 69 | 196–199 (ethyl acetate) |
| 87 | threo-5-[(4-chloro-2-trifluoromethylphenyl)-hydroxymethyl]-4-methoxy-2(5H)-furanone | e | 76 | 166–172 (ethyl acetate) |
| 88 | threo-5-(4-bromo-2-chlorophenyl)-hydroxymethyl-4-methoxy-2(5H)-furanone | e | 84 | 173–176 (methanol) |
| 89 | threo-5-(2-chlorophenylhydroxymethyl)-4-methoxy-5-methyl-2(5H)-furanone | * | 10 | 181–184 (ethyl acetate) |
| 90 | threo-5-(2,6-dimethylphenylhydroxymethyl)-4-methoxy-2(5H)-furanone | d | 36 | 152–153 (dichloromethane/pentane) |
| 91 | threo-5-(2,4-difluorophenylhydroxymethyl)-4-methoxy-2(5H)-furanone | d | 26 | 164 (dichloromethane) |
| 92 | threo-5-(4-bromophenylhydroxymethyl)-4-methoxy-2(5H)-furanone | d | 82 | 157–158 (CCl$_4$/ethyl acetate) |
| 93 | threo-4-methoxy-5-(2-methylphenylhydroxymethyl)-2(5H)-furanone | d | 61 | 174–176 (dichloromethane) |
| 94 | threo-4-methoxy-5-(3-methylphenylhydroxymethyl)-2(5H)-furanone | d | 65 | 127–130 (dichloromethane/pentane) |
| 95 | threo-4-methoxy-5-(4-methylphenylhydroxymethyl)-2(5H)-furanone | e | 71 | 148–151.5 (isopropanol/pentane) |
| 96 | threo-5-(3-fluorophenylhydroxymethyl)-4-methoxy-2(5H)-furanone | d | 82 | 123–126 (dichloromethane/pentane) |
| 97 | threo-5-(4-fluorophenylhydroxymethyl)-4-methoxy-2(5H)-furanone | d | 70 | 141 (toluene/tert.-butyl methyl ether) |
| 98 | threo-5-(3-chlorophenylhydroxymethyl)-4-methoxy-2(5H)-furanone | d | 62 | 150–152 (chloroform/pentane) |
| 99 | threo-4-methoxy-5-(4-nitrophenylhydroxymethyl)-2(5H)-furanone | d | 47 | 226–228 (isopropanol) |
| 100 | threo-5-(2-chloro-6-fluorophenylhydroxymethyl)-4-methoxy-2(5H)-furanone | d | 60 | 129–133 (CCl$_4$/pentane) |
| 101 | threo-5-(2,6-dichlorophenylhydroxymethyl)-4-methoxy-2(5H)-furanone | d | 72 | 176–180 (toluene/acetone) |

*oxidation with sodium chlorate in tert. butanol/water in reflux

EXAMPLE 102 threo-5-[N-benzyloxycarbonyl-L-prolyloxy-(2-chlorophenyl)-methyl]-4-methoxy-2(5H)-furanone; diastereomers A and B To the mixture of 102 g (0.4 M) threo-5-(2-chlorophenylhydroxymethyl)-4-methoxy-2(5H)-furanone, 100 g(0.4 M)N-benzyloxycarbonyl-L-proline and 1200 ml anhydrous dichloromethane whilst stirring and cooling to about −5° C. are added consecutively 6 g (0.04 mole) 4-pyrrolidinopyridine and in portions a total of 91 g (0.44 mole) N,N′-dicyclohexylcarbodiimide. Stirring is then carried out for 4 hours at 0° C., the precipitated N,N′-dicyclohexyl urea filtered off, the filtrate washed twice with 100 ml 5% acetic acid and twice with 100 ml water, dried over anhydrous sodium sulfate and evaporated. The oily crude product is taken up in 1500 ml acetone, allowed to stand for about 15 hours at −8° C. and the remaining N,N′-dicyclohexyl urea filtered off. The filtrate is evaporated, taken up in 250 ml ethanol and allowed to stand for 18 hours at 5° C. The crystallizate precipitating is filtered by suction and recrystallized twice from ethanol. 84.2 g (173 mmole) of the diastereomer A of the title compound with m.p. 164°-167° C. and TLC-Rf=0.53 (n-butanol) is obtained. Yield: 43.3% $[\alpha]_D^{20}$ −16.6 (c=1; methanol).

Analysis: $C_{25}H_{24}ClNO_7$ (485.93) calc.: C(61.79), H (4,98), N (2.88), Cl (7.30) found: C(61.62), H (4.85), N (2.81), Cl (7.6).

To recover the diastereomer B of the title compound the combined ethanolic mother liquors are evaporated, crystallized from isopropanol or n-butanol and recrystallized twice from isopropanol. 72.0 g (148.2 mmole) of the diastereomer B is obtained with m.p. 112°-115° C. and TLC-Rf=0.6 (n-butanol). Yield: 37% $[\alpha]_D^{20}$ −61.3 (c=1; methanol)

Analysis: $C_{25}H_{24}ClNO_7$ (485.93) calc.: C(61.79), H (4.98), N(2.88), Cl (7.30) found: C(61.78), H (4.93), N(2.85), Cl (7.6)

EXAMPLE 103 threo-5-[2-chlorophenyl-(L-prolyloxy)-methyl]-4-methoxy-2(5H)-furanone hydrobromide; diastereomers A and B

A:

48.6 g (100 mmole) of the diastereomer A of Example 102 are suspended in 800 ml ethyl acetate. While stirring and with ice bath cooling, 50 ml 33% hydrogen bromide solution in glacial acetic acid are added dropwise and the mixture allowed to stand for 3 days at about 20° C. The crystallizate is filtered off by suction, washed acid free with ethyl acetate and dried in a vacuum. 36.8 g (85 mmole) of the diastereomer A of the title compound is obtained in the form of the hydrobromide with m.p. 223°-225° C. (decomp.) and TLC-Rf=0.63 (chloroform/methanol 6/4). Yield: 85% . $[\alpha]_D^{20}$ −3.0 (c=1; methanol).

Analysis: $C_{17}H_{18}ClNO_5 \times HBr$ (432.71) calc.: C (47.19), H (4.43), N (3.24), Cl (8.19),Br(18.47) found: C (47.43), H (4.38), N (3.10), Cl (8.1), Br(18.7)

300 MHz - $^1H$—NMR (DMSO—$d_6$); 9.24 very wide, NH-pro), 743-7.65 (4 H, m, aroma. protons), 6.40 (1 H, d, $J_{\alpha/5}$=2.65 Hz, H-α), 5.58 (1 H, d, $J_{3/5}$=0.88 Hz, H-3), 5.4Z (1 H, dd, H-5), 461 (1 H, dd, $J_1$=7.08 Hz, $J_2$=6.63 Hz, H-2-pro), 3.91 (3 H, s, 4-OCH$_3$), 3.1-3.5 (2 H, m, 2 H-5-pro), 2.25-2.35 (1 H, m, H-3a-pro), 1.85-2.03 (3 H, m, H-3b-pro and 2 H-4-pro).

No signals of the diastereomer B can be detected $^1H$-NMR-spectroscopically. The absolute configuration is determined by X-ray diffraction at the monocrystal and is R at C-4 and S at C-α.

B:

47.9 g (98.6 mmole) of the diastereomer B of Example 102 is mixed as described under No. 103 A in 450 ml ethyl acetate with 48 ml 33% hydrobromic acid in glacial acetic acid and processed after being allowed to stand overnight. 40.6 g (93.8 mmole) of the diastereomer B of the title compound is obtained in the form of the hydrobromide with m.p. 190°-193° C. (decomp.) and TLC-Rf=0.54 (chloroform/methanol 6/4).

Yield: 95.2%. $[\alpha]_D^{20}$ −33.5 (c=1; methanol) Analysis: $C_{17}H_{18}ClNO_5 \times HBr$ (432.71) calc : C(47.19), H(4.43), N(3.24), Cl(8.19), Br(18.47) found' C(47.38), H(4.36), N(3.27), Cl(7.8), Br 18.1 )

300 MHz - (DMSO-$d_6$) 9.32 (very wide, NH-pro), 7.4-7.56 (4 H, m, arom. protons), 6.36 (1 H, d, $J_{\alpha/5}$=3.54 Hz, H-α), 5.52 (1 H, s, H-3), 5.38 (1 H, d, H-5), 4.53 (1 H, t, $J_1$=7.96 Hz, $J_2$=6.52 Hz, H-2-pro), 3.89 3 H, s, 4-OCH$_3$), 3.22 (2 H, t, $J_{5/4}$=7.80 Hz, 2 H-5-pro), 2.27-2.40 (1 H, m, H-3a-pro), 1.75-2.05 (3 H, m, H-3b-pro and 2 H-4-pro).

The $^1H$-NMR-spectrum also shows the presence Of about 5% of the diastereomer 103 A (ratio of the integrals of the respective 4-OCH$_3$-protons).

EXAMPLE 104 threo-5-[2-chlorophenyl-(L-prolyloxy)-methyl]-4-methoxy-2(5H)-furanone hydrochloride; diastereomers A and B Analogously to Example 102, 28 g (110 mmole) threo-5-(2-chlorophenylhydroxymethyl)-4-methoxy-2(5H)-furanone is esterified at −5° C. in 500 ml dichloromethane with 23.7 g (110 mmole) N-tert. butoxycarbonyl-L-proline with addition of 1.63 g (11 mmole) 4-pyrrolidinopyridine and 25.2 g (122 mmole) N,N′-dicyclohexylcarbodiimide and processed. 50.1 g of a mixture of the two diastereomeric N-benzyloxycarbonyl-L-prolylesters is obtained, dissolved in 300 ml ethyl acetate and mixed with 18 ml 36% hydrochloric acid with ice bath cooling and stirring. This is allowed to stand for 18 hours at about 20° C. The product which crystallizes out is filtered off by suction and after recrystallization from methanol and drying in vacuum gives 11.57 g (29.8 mmole) of the diastereomer A of the title compound in the form of the hydrochloride with m.p. 213°-214° C.

Yield: 27.1%. $[\alpha]_D^{20}$ −4.2 (c=1; methanol) Analysis: $C_{17}H_{18}ClNO_5 \times HCl$ (388.26) calc.: C(52.59), H(4.93), N(3.61), Cl(18.26) found: C(52.44), H(4.94), N(3.61), Cl(18.3 ).

The filtrate of the hydrolysis mixture is evaporated and after recrystallization from isopropanol and drying in vacuum gives 11.7 g (30.1 mmole) of the diastereomer B of the title compound in the form of the hydrochloride with m.p. 190°-191° C. Yield: 27.4%.$[\alpha]_D^{20}$ −39.4 (c=1; methanol).

Analysis $C_{17}H_{18}ClNO_5 \times HCl$ (388.26) calc.: C(52.59), H(4.93), N(3.61), Cl(18.26) found: C(52.34), H(4.94), N(3.52), Cl(18.1 )

EXAMPLE 105 threo-5-[glycyloxy-(phenyl)-methyl]-4-methoxy-2(5H)-furanone hydrobromide

To the mixture of 44.0 g (200 mmole) threo-4-methoxy-5-phenylhydroxymethyl-2(5H)-furanone, 42.0 g (201 mmole) N-benzyloxycarbonylglycine, 1 liter anhydrous dichloromethane and 3.0 g (20 mmole) 4-pyrrolidinopyridine is added in while stirring and cooling to $-5°$ C., a total of 45.8 g (222 mmole) N,N'-dicyclohexylcarbodiimide and stirring continued until complete esterification. After processing analogously to Example 102, threo-5-[N-benzyloxycarbonylglycyloxy-(phenyl)-methyl]-4-methoxy-2(5H)-furanone is obtained as non-crystallizable oil in quantitative yield. Said oil is mixed in 800 ml ethyl acetate with ice cooling with 100 ml 33% hydrobromic acid in glacial acetic acid. After allowing to stand overnight the crystallisate is sucked off, washed free of acid with ethyl acetate and dried in vacuum. 63.6 g (177.5 mmole) of the title compound is obtained in the form of the hydrobromide with m.p. $204°-205°$ C. and TLC-Rf(chloroform/methanol 6/4)=0.48. Yield: 88.9% Analysis: $C_{14}H_{15}NO_5 \times HBr$ (358.21) calc. C(46.94), H(4.50), N(3.91), Br(22.31) found: C(46.93), H(4.50), N(3.88), Br(21.0)

EXAMPLE 106 threo-5-[N-acetylglycyloxy-(2-chlorophenyl)-methyl]-4-methoxy-2(5H)-furanone:

Analogously to Example 102, to the mixture of 25.5 g (100 nmole) threo-5-(2-chlorophenylhydroxymethyl)-4-methoxy-2(5H)-furanone, 11.8 g (100 mmole) N-acetylglycine, 400 ml anhydrous dichloromethane and 1.5 g (10 mmole) 4-pyrrolidinopyridine at $-5°$ C. is added dropwise the solution of 21.7 g (105 mmole) N,N'-dicyclohexylcarbodiimide in 100 ml dichloromethane and then stirred for 4 hours at $-5°$ C. The crude product gives after recrystallization from ethanol and then from isopropanol 19.5 g (55.1 mmole) of the title compound with m.p. $160°-162°$ C. and TLC-Rf(chloroform/methanol 95/5)=0.45. Yield: 55.1%.

Analysis: $C_{16}H_{16}ClNO_6$ (353.77) calc.: C(54.32), H(4.56), N(3.96), Cl(10.02) found: C(53.46), H(4.39), N(3.80), Cl(10.0).

EXAMPLE 107 threo-5-[N-acetyl-L-prolyloxy-(2-chlorophenyl)-methyl]-4-methoxy-2(5H)-furanone; diastereomer A To the mixture of 100 ml anhydrous dichloromethane, 4.0 ml (50 mmole) pyridine and 0.3 g (2 mmole) 4-pyrrolidinopyridine, while stirring and ice bath cooling are added in succession 8.65 g (20 mmole) threo-5-[2-chlorophenyl-(L-prolyloxy)-methyl]-4-methoxy-2(5H)-furanone hydrobromide (diastereomer A from Example 103) and 2.8 ml (30 mmole) acetic anhydride, then stirring for 2.5 hours at $0°$ C. This is washed free from pyridine with ice water, the dichloromethane phase dried over anhydrous sodium sulfate, evaporated and the product crystallized by treating with anhydrous ethanol. Recrystallization from ethanol gives 6.79 g (17.2 mmole) of the title compound with m.p. $168°-170°$ C. and TLC-Rf (chloroform/methanol 6/4)=0.77. Yield: 86.2%. $[\alpha]_D^{20} -33$ (c=1; methanol).

Analysis: $C_{19}H_{20}ClNO_6$ (393.83) calc.: C(57.95), H(5.12), N(3.56), Cl(9.00) found: C(57.72), H(5.20), N(3.45), Cl(9.2)

The following amino acid ester derivatives are obtained analogously to the procedures described in Examples 102 to 107. The respective empirical formulae given correspond to the results of the elementary analyses.

EXAMPLE 108 threo-4-methoxy-5-[phenyl-(L-phenylglycyloxy)-methyl]-2(5H)-furanone hydrobromide; diastereomers A and B Preparation by esterification of threo-4-methoxy-5-phenylhydroxymethyl-2(5H)-furanone with N-benzyloxycarbonyl-L-phenylglycine and subsequent splitting off of the protective group with HBr/glacial acetic acid.

Diastereomer A:
$C_{20}H_{19}NO_5 \times HBr$ (434.30), m.p. $208°-210°$ C. (decomp.,from isopropanol/pentane); TLC-Rf (chloroform/methanol 6/4)=0.78.
$[\alpha]_D^{20} +56.4$ (c=1; methanol).
The product contains according to the $^1$H-NMR-spectrum about 27% of the diastereomer B. Yield: 13.4%.

Diastereomer B: $C_{20}H_{19}NO_5 \times HBr$ (434.30), m.p. $218°-219°$ C. (decomp., from isopropanol/ethanol 2/1). TLC-Rf (chloroform/methanol 6/4)=0.70.
$[\alpha]_D^{20} +29.8$ (c=1; methanol). Yield: 31.3% No diastereomer A can be detected $^1$H-NMR spectrometrically.

EXAMPLE 109 threo-5-[N-benzyloxycarbonyl-L-prolyloxy-(phenyl)-methyl]-4-methoxy-2(5H)-furanone; diastereomers A and B Preparation by esterification of threo-4-methoxy-5-phenylhydroxymethyl-2(5H)-furanone with N-benzyloxycarbonyl-L-proline.

Diastereomer A:
$C_{25}H_{25}NO_7$ (451.49), m.p. $138.5°-139.5°$ C. (from ethanol); TLC-Rf (toluene/acetone 8/2)=0.31. $[\alpha]_D^{20} -3.3$ (c=1; methanol). Yield: 36.9%

Diastereomer B:
$C_{25}H_{25}NO_7$ (451 49), m.p. $88°-92°$ C. ($2\times$ from isopropanol); TLC-Rf (toluene/acetone 8/2)=0.33. $[\alpha]_D^{20} -89.8$ (c=1; methanol). Yield: 20.9%

EXAMPLE 110 threo-4-methoxy-5-[phenyl-(1-prolyloxy)-methyl]-2(5H)furanone hydrobromide; diastereomers A and B Preparation by splitting off of the protective group from the diastereomers A and B of Example 109 by means of HBr/glacial acetic acid.

Diastereomer A:
$C_{17}H_{19}NO_5 \times HBr$ (398.27), m.p. $185°$ C. (from ethyl acetate). TLC-Rf (chloroform/methanol 6/4)=0.58 $[\alpha]_D^{20} +18.2$ (c=1; methanol). Yield: 85.1%.

Diastereomer B:
$C_{17}H_{19}NO_5 \times HBr$ (398.27) m.p. $191°-194°$ C. (from ethanol). TLC-Rf (chloroform/methanol 6/4)=0.54. $[\alpha]_D^{20} -71.3$ (c=1; methanol). Yield: 85.4%

EXAMPLE 111 threo-5-[2-chlorophenyl-(glycyloxy)-methyl]-4-methoxy-2(5H)-furanone hydrobromide:

Preparation by esterification of threo-5-(2-chlorophenylhydroxymethyl)-4-methoxy-2(5H)-furanone with N-benzyloxycarbonylglycine and subsequent splitting off of the protective group.

$C_{14}H_{14}ClNO_5 \times HBr$ (392.65). m.p. 202°–205° C. (from isopropanol/ethanol 2/1). TLC-Rf (chloroform/methanol 6/4)=0.58. Yield: 62.6%.

EXAMPLE 112 threo-5-[2-chlorophenyl-glycyloxy)methyl-4-methoxy-2(5H)-furanone hydrochloride:

Obtained from the hydrobromide of Example 111 by conversion to the hydrochloride.

$C_{14}H_{14}ClNO_5 \times HCl$ (348.20). m.p. 188°–189° C. (from isopropanol/methanol). Yield: 89.3%

EXAMPLE 113 threo-5-[4-aminobutanoyloxy-(2-chlorophenyl)-methyl]-4-methoxy-2(5H)-furanone hydrobromide:

Preparation by esterification of threo-5-(2-chlorophenyl-hydroxymethyl)-4-methoxy-2(5H)-furanone with 4-(N-benzyloxycarbonylamino)-butyric acid with subsequent splitting off of the protective group.

$C_{16}H_{18}ClNO_5 \times HBr$ (420.70). m.p. 181°–182° C. (from ethanol). TLC-Rf (chloroform/methanol 6/4)=0.5. Yield: 78.5%

EXAMPLE 114 threo-5-[4-aminobutanoyloxy-(2-chlorophenyl)-methyl]-4-methoxy-2(5H)-furanone hydrochloride:

Prepared by converting the hydrobromide of Example 113 to hydrochloride.

$C_{16}H_{18}ClNO_5 \times HCl$ (376.25). m.p. 165°–169° C. (from isopropanol).

EXAMPLE 115 threo-5-[4-(N-acetylamino)-butanoyloxy-(2-chlorophenyl)methyl]-4-methoxy-2(5H)-furanone:

Prepared by acetylation of the substance of Example 113.

$C_{18}H_{20}ClNO_6$ (381.82). Vitreous product (from isopropanol). TLC-Rf (chloroform/methanol 95/5)=0.35. Yield: 91%.

EXAMPLE 116 threo-5-[N-benzyloxycarbonyl-L-phenylglycyloxy (2-chlorophenyl)-methyl]-4-methoxy-2(5H)-furanone Preparation by esterification of threo-5-(2-chlorophenylhydroxymethyl)-4-methoxy-2(5H)-furanone with N-benzyloxycarbonyl-L-phenylglycine.

After recrystallization from ethanol a mixture of the two diastereomers A and B is obtained.

$C_{28}H_{24}ClNO_7$ (521.96). m.p. 137°–140° C. $[\alpha]_D^{20}+32.4$ (c=1; methanol) Yield: 74.6%.

EXAMPLE 117 threo-5-[2-chlorophenyl-(L-phenylglycyloxy)-methyl]-4-methoxy-2(5H)-furanone hydrobromide; diastereomers A and B Preparation by splitting off the protective group from the substance of Example 116 and subsequent fractional crystallization.

Diastereomer A:

$C_{20}H_{18}ClNO_5 \times HBr$ (468.74). m.p. 215° C. (decomp.; from ethanol/pentane), TLC-Rf (chloroform/methanol 9/1)=0.64. $[\alpha]_D^{20}+47.3$ (c=1; methanol). Yield: 22.8%

Diastereomer B:

$C_{20}H_{18}ClNO_5 \times HBr$ (468.74). Decomposition range 138°–180° C. from isopropanol . TLC-Rf (chloroform/methanol 9/1)=0.54. $[\alpha]_D^{20}+0.9$ (c=1; methanol). Yield: 9.9%.

EXAMPLE 118 threo-5-[N-benzyloxycarbonyl-D-phenylglycyloxy-(2-chlorophenyl)-methyl]-4-methoxy-2(5H)-furanone Preparation analogously to Example 116 by esterification with N-benzyloxycarbonyl-D-phenylglycine. A mixture of the two diastereomers A and B is obtained after recrystallization from ethanol.

$C_{28}H_{24}ClNO_7$ (521.96). m.p. 137°–140° C. $[\alpha]_D^{20}-32.0$ (c=1; methanol). Yield: 75.3%.

EXAMPLE 119 threo-5-[2-chlorophenyl-(D-phenylglycyloxy)-methyl]-4-methoxy-2(5H)-furanone hydrobromide; diastereomers A and B Preparation by splitting off the protective group from the substance of Example 118 and subsequent fractional crystallization.

Diastereomer A:

$C_{20}H_{18}ClNO_5 \times HBr \times H_2O$ (486.76). m.p. 215° C. (decomp.; from ethanol/pentane). TLC-Rf (chloroform/methanol 9/1)=0.64; $[\alpha]_D^{20}-48.3$ (c=1; methanol). Yield: 25.8%.

Diastereomer B:

$C_{20}H_{18}ClNO_5 \times HBr$ (468.74). Decomposition range: 138°–180° C. (from isopropanol).TLC-Rf (chloroform/methanol 9/1)=0.54. $[\alpha]_D^{20}-0.9$ (c=1; methanol). Yield: 16.4%.

EXAMPLE 120 threo-5-[2-chlorophenyl-(L-phenylalanyloxy)-methyl]-4-methoxy-2(5H)-furanone hydrobromide; diastereomer B Preparation by esterification of threo-5-(2-chlorophenylhydroxymethyl)-4-methoxy-2(5H)-furanone with N-benzyloxycarbonyl-L-phenylalanine and subsequent splitting off of the protective group by means of HBr/glacial acetic acid in ethyl acetate. As first crystallizate, the diastereomer B is obtained in the form of the hydrobromide. $C_{21}H_{20}ClNO_5 \times HBr$ (482.77). m.p. 139°–143° C. (3 times from ethyl acetate). TLC-Rf (chloroform/methanol 95/5)=0.30. $[\alpha]_D^{20}-3.2$ (c=1; methanol). Yield: 11.3%. Diastereomer A: see following Example.

EXAMPLE 121 threo-5-[2-chlorophenyl-(N-isopropylidene-L-phenylalanyloxy) -methyl]-4-methoxy-2(5H)-furanone hydrobromide; diastereomers A and B The filtrate of the first crystallizate from Example 120 is evaporated, dissolved in acetone and allowed to stand for 25 hours at −6° C. The diastereomer A precipitates in crystalline form as hydrobromide of the N-isopropylidene derivative.

$C_{24}H_{24}ClNO_5 \times HBr$ (522.84). m.p. 192°–193° C.(decomp.; twice from methanol). TLC-Rf (chloroform/methanol 95/5) =0.43. $[\alpha]_D^{20}-16$ (c=1: methanol). Yield: 28.4%.

If the diastereomer B from Example 120 is heated in acetone the corresponding N-isopropylidene derivative B is also obtained.

$C_{24}H_{24}ClNO_5 \times HBr$ (522.84). m.p. 180°–183° C. (decomp.; from acetone). TLC-Rf (chloroform/methanol 95/5)=0.32. $[\alpha]_D^{20}$ −31.9 (c=1: methanol).

EXAMPLE 122 threo-5-[2-chlorophenyl-(L-glutaminyloxy)-methyl]-4-methoxy-2(5H)-furanone hydrobromide; diastereomer A Preparation by esterification of threo-5-(2-chlorophenylhydroxymethyl)-4-methoxy-2(5H)-furanone with N-benzyloxycarbonyl-L-glutamine and subsequent splitting off of the protective group with HBr/glacial acetic acid.

Diastereomer A:
$C_{17}H_{19}ClN_2O_6 \times HBr \times H_2O$ (481.74). m.p. 186°–188° C. (decomp; twice from isopropanol/ethanol). TLC-Rf (chloroform/methanol 6/4)=0.35. $[\alpha]_D^{20}$ +21.4 (c=0.5; methanol). Yield: 16.2%.

Diastereomer B was not isolated.

EXAMPLE 123 threo-5-[2-chlorophenyl-(α-L-glutamyloxy)-methyl]-4-methoxy-2(5H)-furanone hydrobromide; diastereomer A Preparation by esterification of threo-5-(2-chlorophenylhydroxymethyl)-4-methoxy-2(5H)-furanone with N-benzyloxycarbonyl-L-glutamic acid-5-tert. butyl ester and subsequent splitting off of the N-benzyloxycarbonyl and of the tert. butoxy protective group.

Diastereomer A:
$C_{17}H_{18}ClNO_7 \times HBr$ (464.71). m.p. 190°–194° C. (twice from isopropanol).TLC-Rf (chloroform/methanol 6/4)=0.16 $[\alpha]_D^{20}$ +11.1 (c=1; methanol). Yield: 25.2%.

Diastereomer B was not isolated.

EXAMPLE 124 threo-5-[N-acetyl-L-methionyloxy(2-chlorophenyl)-methyl]-4-methoxy-2(5H)-furanone; diastereomer A Preparation by esterification of threo-5-(2-chlorophenylhydroxymethyl)-4-methoxy-2(5H)-furanone with N-acetyl-L-methionine.

Diastereomer A:
$C_{19}H_{22}ClNO_6S$ (427.91). m.p. 107°–110° C. (twice from ethyl acetate/pentane). TLC-Rf (toluene/acetone 6/4)=0.53. $[\alpha]_D^{20}$ −0.7 (c=1; methanol). Yield: 12%.

Diastereomer B was not isolated.

EXAMPLE 125 threo-5-[2-chlorophenyl-(5-oxo-L-prolyloxy)-methyl]-4-methoxy-2(5H)-furanone; diastereomers A and B Preparation by esterification of threo-5-(2-chlorophenylhydroxymethyl)-4-methoxy-2(5H)-furanone with 5-oxo-L-proline and separation of the diastereomers by means of column chromatography on silica with chloroform/methanol 98/2 as eluent.

Diastereomer A:
$C_{17}H_{16}ClNO_6$ (365.78). Decomposition range 75°–130° C. (from tert. butylmethylether). TLC-Rf (chloroform/methanol 95/5)=0.37. $[\alpha]_D^{20}$ +4.0 (c=1; methanol).

Diastereomer B:
$C_{17}H_{16}ClNO_6$ (365.78) m.p. 135°–145° C. (from dichloromethane/pentane). TLC-Rf (chloroform/methanol 95/5)=0.29. $[\alpha]_D^{20}$ −2.7 (c=1; methanol).

EXAMPLE 126 threo-5-[N-benzyloxycarbonyl-L-prolyloxy-(2-bromophenyl)-methyl]-4-methoxy-2(5H)-furanone; diastereomers A and B Preparation by esterification of threo-5-(2-bromophenylhydroxymethyl)-4-methoxy-2(5H)-furanone with N-benzyloxycarbonyl-L-proline.

Diastereomer A:
$C_{25}H_{24}BrNO_7$ (530.39). m.p. 136°–137° C. (from isopropanol). TLC-Rf (toluene/acetone 8/2)=0.28. $[\alpha]_D^{20}$ −26.2 (c=1; methanol). Yield: 37.2%

Diastereomer B:
$C_{25}H_{24}BrNO_7$ (530.39). m.p. 106°–109° C. (from isopropanol/tert. butylmethylether). TLC-Rf (toluene/acetone 8/2)=0.32. $[\alpha]_D^{20}$ −46.0 (c=1; methanol). Yield: 7.3%.

A further 47% of a mixture of the two diastereomers was obtained from the mother liquors.

EXAMPLE 127 threo-5-[2-bromophenyl-(L-prolyloxy)-methyl]-4-methoxy-2(5H)-furanone hydrobromide; diastereomers A and B Preparation by splitting off the protective group from the substances of Example 126 by means of HBr/glacial acetic acid.

Diastereomer A:
$C_{17}H_{18}BrNO_5 \times HBr$ (477.17). m.p. 222°–224° C. (from ethyl acetate). TLC-Rf (butanol; polygram Sil G)=0.12. $[\alpha]_D^{20}$ −12.3 (c=1; methanol). Yield: 94.4%.

Diastereomer B:
$C_{17}H_{18}BrNO_5 \times HBr$ (477.17). m.p. 191°–193° C. (from ethyl acetate). TLC-Rf (butanol; polygram Sil G)=0.09. $[\alpha]_D^{20}$ −22.4 (c=1: methanol). Yield: 60%.

EXAMPLE 128 threo-5-[N-benzyloxycarbonyl-L-prolyloxy-(2-fluorophenyl)-methyl]-4-methoxy-2(5H)-furanone; diastereomers A and B Preparation by esterification of threo-5-(2-fluorophenylhydroxymethyl)-4-methoxy-2(5H)-furanone with N-benzyloxycarbonyl-L-proline.

Diastereomer A:
$C_{25}H_{24}FNO_7$ (469.48). m.p. 169°–171° C. (from methanol). TLC-Rf (toluene/acetone 8/2)=0.25. $[\alpha]_D^{20}$ +2.0 (c=1; methanol). Yield: 27.7%.

Diastereomer B:
$C_{25}H_{24}FNO_7$ (469.48). m.p.138°–140° C. (from ethanol). TLC-Rf (toluene/acetone 8/2)=0.29. $[\alpha]_D^{20}$ −84.3 (c=1; methanol). Yield: 30.2%.

A further 17.3% of a mixture of the two diastereomers was obtained from the mother liquors.

EXAMPLE 129 threo-5-[2-fluorophenyl-(L-prolyloxy)-methyl]-4-methoxy-2(5H)-furanone hydrobromide; diastereomers A and B Preparation by splitting off of the protective group from the substances of Example 128.

Diastereomer A:
$C_{17}H_{18}FNO_5 \times HBr$ (416.26). m.p. 208°–210° C. (decomp.; from ethanol). TLC-Rf (chloroform/methanol 9/1)=0.34. $[\alpha]_D^{20}$ +15.4 (c=0.57; methanol). Yield: 87.5%.

Diastereomer B:

$C_{17}H_{18}FNO_5 \times HBr$ (416.26). m.p.175°–180° C. (from ethanol). TLC-Rf (chloroform/methanol 9/1)=0.31. $[\alpha]_D^{20}$ −58.8 (c=0.57; methanol). Yield: 77.6%.

EXAMPLE 130 threo-5-[2,4-dichlorophenyl-(glycyloxy)-methyl]-4-methoxy-2(5H)-furanone hydrobromide Preparation by esterification of threo-5-(2,4-dichlorophenylhydroxymethyl)-4-methoxy-2(5H)-furanone with N-benzyloxycarbonylglycine and subsequent splitting off of the protective group by means of HBr/glacial acetic acid. $C_{14}H_{13}Cl_2NO_5 \times HBr$ (427.10). m.p. 222°–223° C. (from ethanol). TLC-Rf (chloroform/methanol 6/4)=0.57. Yield: 79.1%.

EXAMPLE 131 threo-5-[2,4-dichlorophenyl-(glycyloxy)-methyl]-4-methoxy-2(5H)-furanone hydrochloride Preparation by conversion of the hydrobromide from Example 130 to the hydrochloride.

$C_{14}H_{13}Cl_2NO_5 \times HCl$ (382.64). m.p. 206°–208° C. (twice from methanol/isopropanol).

EXAMPLE 132 threo-5-[N-acetylglycyloxy-(2,4-dichlorophenyl)-methyl]-4-methoxy-2(5H)-furanone Preparation by esterification of threo-5-(2,4-dichlorophenylhydroxymethyl)-4-methoxy-2(5H)-furanone with N-acetylglycine.

$C_{16}H_{15}Cl_2NO_6$ (388.22). m.p. 197°–198° C. (twice from ethanol). TLC-Rf (chloroform/methanol 95/5)=0.27. Yield: 49.7%.

EXAMPLE 133 threo-5-[L-alanyloxy-(2,4-dichlorophenyl)-methyl]-4-methoxy-2(5H)-furanone hydrobromide Preparation by esterification of threo-5-(2,4-dichlorophenylhydroxymethyl)-4-methoxy-2(5H)-furanone with N-benzyloxycarbonyl-L-alanine and subsequent splitting off of the protective group. After crystallization from ethyl acetate a mixture of the diastereomers A and B was obtained which was not further separated.

$C_{15}H_{15}Cl_2NO_5 \times HBr$ (441.19). m.p. 173°–175° C. TLC-Rf (chloroform/methanol 6/4)=0.6. $[\alpha]_D^{20}$+0.9 (c=1; methanol). Yield: 79.8%.

EXAMPLE 134 threo-5-[N-benzyloxycarbonyl-L-prolyloxy-(2,4-dichlorophenyl)-methyl]-4-methoxy-2(5H)-furanone. Diastereomers A and B Preparation by esterification of threo-5-(2,4-dichlorophenylhydroxymethyl)-4-methoxy-2(5H)-furanone with N-benzyloxycarbonyl-L-proline.

Diastereomer A:
$C_{25}H_{23}Cl_2NO_7$ (520.38). m.p. 111°–113° C. (from ethanol). TLC-Rf (chloroform/methanol 6/4)=0.74. $[\alpha]_D^{20}$+19.9 (c=1; methanol). Yield: 33%.

Diastereomer B:
$C_{25}H_{23}Cl_2NO_7$ (520.38). m.p. 117°–119° C. (from ethanol). TLC-Rf (toluene/tert. butylmethylether 7/3)=0.16. $[\alpha]_D^{20}$: −83.9 (c=1; methanol). Yield: 28.4%.

EXAMPLE 135 threo-5-[2,4-dichlorophenyl-(L-prolyloxy)-methyl]-4-methoxy-2(5H)-furanone hydrobromide; diastereomers A and B Preparation by splitting off of the protective group from the substances of Example 134 by means of HBr/glacial acetic acid.

Diastereomer A:
$C_{17}H_{17}Cl_2NO_5 \times HBr$ (467.16). m.p. 198°–200° C. (from ethyl acetate). TLC-Rf (chloroform/methanol 95/5)=0.26. $[\alpha]_D^{20}$+20.2 (c=1; methanol). Yield: 87.7%.

Diastereomer B:
$C_{17}H_{17}Cl_2NO_5 \times HBr$ (467.16). m.p. 179°–180° C. (from ethyl acetate/n-hexane). TLC-Rf (chloroform/methanol 95/5)=0.26. $[\alpha]_D^{20}$−55.8 (c=1; methanol). Yield: 90.8%.

EXAMPLE 136 threo-5-[N-benzyloxycarbonyl-L-prolyloxy-(2,5-dichlorophenyl)-methyl]-4-methoxy-2(5H)-furanone; diastereomers A and B Preparation by esterification of threo-5-(2,5-dichlorophenylhydroxymethyl)-4-methoxy-2(5H)-furanone with N-benzyloxycarbonyl-L-proline.

Diastereomer A:
$C_{25}H_{23}Cl_2NO_7$ (520.38). m.p. 90°–94° C. (twice from isopropanol/n-hexane). TLC-Rf (n-butanol)=0.55. $[\alpha]_D^{20}$+7.9 (c=0.5; methanol).

Diastereomer B:
$C_{25}H_{23}Cl_2NO_7$ (520.38). m.p. 90°–95° C. (from butanol/n-pentane). TLC-Rf (n-butanol)=0.60. $[\alpha]_D^{20}$−55.8 (c=0.5; methanol).

EXAMPLE 137 threo-5-[2,5-dichlorophenyl-(L-prolyloxy)-methyl)4-methoxy-2(5H)-furanone hydrobromide; diastereomers A and B Preparation by splitting off of the protective groups from the substances of Example 136 by means of HBr/glacial acetic acid.

Diastereomer A:
$C_{17}H_{17}Cl_2NO_5 \times HBr$ (467.16). m.p. 200°–202° C. (from ethanol). TLC-Rf (chloroform/methanol 6/4)=0.68 $[\alpha]_D^{20}$+16.3 (c=1; methanol). Yield: 91.4%.

Diastereomer B:
$C_{17}H_{17}Cl_2NO_5 \times HBr$ (467.16). m.p. 171°–173° C. (from ethyl acetate). TLC-Rf (chloroform/methanol 95/5)=0.3. $[\alpha]_D^{20}$−56.7 (c=1; methanol).

EXAMPLE 138 threo-5-[N-benzyloxycarbonyl-L-prolyloxy-(2-trifluoromethylphenyl)-methyl]-4-methoxy-2(5H)-furanone; diastereomers A and B Preparation by esterification of threo-4-methoxy-5-(2-trifluoromethylphenylhydroxymethyl)-2(5H)-furanone with N-benzyloxycarbonyl-L-proline.

Diastereomer A:
$C_{26}H_{24}F_3NO_7$ (519.49). m.p. 136°–138° C. (from isopropanol). TLC-Rf (toluene/acetone 8/2)=0.33. $[\alpha]_D^{20}$+10.2 (c=0.5; methanol). Yield: 27.7%.

Diastereomer B:
$C_{26}H_{24}F_3NO_7$ (519.49)
Fraction 1: m.p 95°–100° C. (from isopropanol/pentane).TLC-Rf (toluene/acetone 8/2)=0.35.

$[\alpha]_D^{20}-53.0$ (c=0.5; methanol). Yield: 20.8% (still contains diastereomer A).

Fraction 2: m.p. 108°–113° C. $[\alpha]_D^{20}-79.4$ (c=0.5; methanol). Yield: 0.4% (TLC:diastereomer-pure).

Fraction 3: m.p. 114°–121° C. $[\alpha]_D^{20}-60.4$ (c=0.5; methanol). Yield: 9.6% (still contains diastereomer A).

Fraction 4: Oil. Yield: 33.9%. Mixture of the diastereomers A and B (mainly B).

EXAMPLE 139 threo-4-methoxy-5-[L-prolyloxy-(2-trifluoromethylphenyl)-methyl]-2(5H)-furanone hydrobromide; diastereomers A and B Preparation by splitting off of the protective group from the substances of Example 138 by means of HBr/glacial acetic acid.

Diastereomer A:

$C_{18}H_{18}F_3NO_5 \times HBr$ (466.27). m.p. 210°–211° C. (from ethyl acetate) TLC-Rf(chloroform/methanol 6/4)=0.58. $[\alpha]_D^{20}+24.2$ (c=0.5; methanol). Yield: 90.2%. Diastereomer purity>97% (determined by $^1$H-NMR spectroscopy).

Diastereomer B:

$C_{18}H_{18}F_3NO_5 \times HBr$ (466.27)

Fraction 1 (acidolysis of fraction 4 from Example 138 B): m.p 192°–194° C. (from ethyl acetate). TLC-Rf (chloroform/methanol 6/4)=0.60. $[\alpha]_D^{20}-72.8$ (c=0.5; methanol). Yield: 19.4%. Diastereomer purity>99% ($^1$H-NMR spectroscopically).

Fraction 2 (acidolysis of fraction 1 from Example 138 B): m.p. 185°–189° C.; $[\alpha]_D^{20}-56.4$ (c=0,5; methanol). Yield: 10.6%. Diastereomer purity=77.5% (By $^1$H-NMR spectroscopy a content of 22.5% diastereomer A is determined).

Fraction 3 (acidloysis of fraction 3 from Example 138 B): m.p. 189°–190° C.; $[\alpha]_D^{20}-48.6$ (c=0.5; methanol). Yield: 87.9% (still contains diastereomer A).

EXAMPLE 140 threo-5-[N-benzyloxycarbonyl-L-prolyloxy-(2-methylphenyl)-methyl]-4-methoxy-2(5H)-furanone. Diastereomers A and B Preparation by esterification of threo-4-methoxy-5-(2-methylphenylhydroxymethyl)-2(5H)-furanone with N-benzyloxycarbonyl-L-proline.

Diastereomer A:

$C_{26}H_{27}NO_7$ (465.52). m.p. 132°–134° C. (from isopropanol). TLC-Rf (toluene/acetone 8/2)=0.31. $[\alpha]_D^{20}+13.8$ (c=0.5; methanol). Yield: 32.2%.

Diastereomer B:

$C_{26}H_{27}NO_7$ (465.52). m.p. 114°–116° C. (from isopropanol/ethanol 1/1). TLC-Rf (toluene/acetone 8/2)=0.41. $[\alpha]_D^{20}-85.8$ (c=0.5: methanol). Yield: 22.0%.

From the mother liquors a mixture of the two diastereomers A and B is obtained with a yield of 38.1%.

EXAMPLE 141 threo-4-methoxy-5-2-methylphenyl-(L-prolyloxy)-methyl]-(2(5H)-furanone hydrobromide; diastereomers A and B Preparation by splitting off of the protective group from the substances of Example 140 by means of HBr/glacial acetic acid.

Diastereomer A:

$C_{18}H_{21}NO_5 \times HBr$ (412.30). m.p. 222°–225° C. (decomp.: from ethyl acetate). TLC-Rf (chloroform/methanol 6/4)=0.58. $[\alpha]_D^{20}+5.8$ (c=0.5; methanol). Diastereomer purity>98%. ($^1$H-NMR spectroscopically). Yield: 70.6%.

From the mother liquor a further diastereomer A with m.p. 221°–223° C. (decomp.) and $[\alpha]_D^{20}+5.0$ (c=0.5; methanol) is obtained with a 25.1% yield.

Diastereomer B:

$C_{18}H_{21}NO_5 \times HBr$ (412.30). m.p. 195°–196° C. (decomp; from ethyl acetate). TLC-Rf (chloroform/methanol 6/4)=0.55. $[\alpha]_D^{20}-58.0$ (c=0.5; methanol). Diastereomer purity>99%. ($^1$H-NMR spectroscopically). Yield: 92.7%.

Acidolysis of the diastereomer mixture from the mother liquor of Example 140 gives a 14.2% yield of diastereomer A with m.p. 219°–220° C. (decomposition; from ethanol) and $[\alpha]_D^{20}+5.0$ (c=0.5; methanol) as well as a 36.2% yield diastereomer B with m.p. 205°–207° C. (decomposition; from ethanol) and $[\alpha]_D^{20}-50.2$ (c=0.5; methanol).

EXAMPLE 142

(+)-threo-5-(2-chlorophenylhydroxymethyl)-4-methoxy-2(5H)-furanone

Process a:

The mixture of 17.3 g (40 mmole) threo-5-[2-chlorophenyl-(L-prolyloxy)-methyl]-4-methoxy-2(5H)-furanone hydrobromide diastereomer A (preparation see Example 103), 1 liter anhydrous methanol and 5.9 g (80 mmole) anhydrous lithium carbonate is stirred for 4 days at 0° C., then mixed with 80 ml 1M hydrochloric acid and concentrated in vacuum to about 150 ml. 300 ml chloroform is added, the chloroform phase extracted with 50 ml 1M hydrochloric acid and 2×50 ml water, dried over anhydrous sodium sulfate and evaporated. After drying at 100° C. in vacuum recrystallization from ethyl acetate/n-pentane gives 4.98 g (19.6 mmole) of the title compound with m.p. 127° C.–128° C. and $[\alpha]_D^{20}+98.0$ (c =0.2; acetone). $C_{12}H_{11}ClO_4$ (254.67). Elementary analysis and $^1$H-NMR spectrum are identical to those of the racemic compound of Example 64. Yield 49%.

Process b:

750 mg (1.73 mmole) threo-5-[2-chlorophenyl-(L-prolyloxy)-methyl]-4-methoxy-2(5H)-furanone hydrobromide diastereomer A are heated in 50 ml water for 16 hours under reflux boiling. After cooling the product which has crystallized out is sucked off. Recrystallization from tetrachloromethane gives 251 mg (0.99 mmole) of the title compound with m.p. 123° C. and $[\alpha]_D^{20}+99.0$ (c=0.25; acetone). Yield 57%.

EXAMPLE 143

(−)-threo-5-(2-fluorophenylhydroxymethyl)-4-methoxy-2(5H)-furanone

The mixture of 12.5 g (30 mmole) threo[-2-fluorophenyl-(L-prolyloxy)-methyl]-4-methoxy-2(5H)-furanone hydrobromide diastereomer B (from Example 129) and 400 ml water is stirred for 20 hours at 85° C. and 2 hours at 100° C. After cooling the product is extracted with 200 ml dichloromethane, the extract washed with 3×70 ml water and the purified washing waters extracted with 100 ml dichloromethane. The purified dichloromethane extracts are evaporated and recrystallized from tert. butylmethyl ether. After drying at 70° C. in vacuum 6.513 g (27.3 mmole) of the title compound is obtained with m.p. 152° C.–154° C. and $[\alpha]_D^{20}-111.8$ (c=0.51; acetone). Yield: 91%.

Analysis: $C_{12}H_{11}FO_4$ (238.22)
calc.: C(60.50), H(4.66), F(7.98)
found: C(60.32), H(4.60), F(8.0)

In a manner analogous to that described in Examples 142 and 143 by acid or base-catalysed cleavage of the corresponding amino acid esters the following optically active threo-4-methoxy-5-phenylhydroxymethyl-2(5H)-furanone derivatives are obtained.

EXAMPLE 144

(−)-threo-5-(2-chlorophenylhydroxymethyl)-4-methoxy-2(5H)-furanone

Preparation from the diastereomer B of Example 103 $C_{12}H_{11}ClO_4$ (254.67). m.p. 125°–126° C. (from water). $[\alpha]_D^{20}-96.6$ (c=0.5; acetone). Yield: 85.6%.

EXAMPLE 145

(+)-threo-4-methoxy-5-phenylhydroxymethyl-2(5H)-furanone

Preparation from the diastereomer A of Example 110 $C_{12}H_{12}O_4$ (220.28). m.p. 160°–163° C. (2×from ethanol/water). $[\alpha]_D^{20}+101.2$ (c=0.5; acetone). Yield: 75.9%.

EXAMPLE 146

(−)-threo-4-methoxy-5-phenylhydroxymethyl-2(5H)-furanone

Preparation from the diastereomer B of Example 110. $C_{12}H_{12}O_4$ (220.28). $[\alpha]_D^{20}-103.6$ (c=0.5; acetone). Yield 64.4%.

EXAMPLE 147

(+)-threo-5-(2-bromophenylhydroxymethyl)-4-methoxy-2(5H)-furanone

Preparation from the diastereomer A of Example 127. $C_{12}H_{11}BrO_4$ (299.13). m.p. 134°–138° C. (from 80% ethanol). $[\alpha]_D^{20}+73.6$ (c=0.5; acetone). Yield: 74.3%.

EXAMPLE 148

(+)-threo-5-(2,4-dichlorophenylhydroxymethyl)-4-methoxy-2(5H)-furanone

Preparation from the diastereomer A of Example 135. $C_{12}H_{10}Cl_2O_4$ (289.12). m.p. 140°–143° C. (from isopropanol). $[\alpha]_D^{20}+118.5$ (c=0.2; acetone). Yield: 69.9%.

EXAMPLE 149

(−)-threo-5-(2,4-dichlorophenylhydroxymethyl)-4-methoxy-2(5H)-furanone

Preparation from the diastereomer B of Example 135. $C_{12}H_{10}Cl_2O_4$ (289.12). m.p. 138°–141° C. (from isopropanol). $[\alpha]_D^{20}-119.5$ (c=0.2; acetone). Yield: 77.5%.

EXAMPLE 150

(+)-threo-5-[N-acetylglcyloxy-(2-chlorophenyl)-methyl-4-methoxy-2(5H)-furanone

Preparation analogous to Example 106 by esterification of (+)-threo-5-(2-chlorophenylhydroxymethyl)-4-methoxy-2(5H)-furanone (for preparation see Example 142) with N-acetylglycine.

$C_{16}H_{16}ClNO_6$ (353.77). m.p. 170°–171° C. (from isopropanol/methanol 1/1). TLC-Rf (chloroform/methanol 95/5)=0.45. $[\alpha]_D^{20}+4.8$ (c=0.5; methanol p.a.). Yield: 63.5%.

EXAMPLE 151

(+)-threo-5-[2-chlorophenyl-(glycyloxy)-methyl]-4-methoxy-2(5H)-furanone hydrobromide To the mixture of 7.64 g (30 mmole) (+)-threo-5-(2-chlorophenylhydroxymethyl)-4-methoxy-2(5H)-furanone (for preparation see Example 142), 6.28 g (30 mmole) N-benzyloxycarbonylglycine and 150 ml anhydrous dichloromethane, with stirring and cooling to −5° C., are added in succession 0.3 g (2 mmole) 4-pyrrolidinopyridine and the solution of 6.8 g (33 mmole) dicyclohexylcarbodiimide in 30 ml anhydrous dichloromethane. After stirring for 4 hours at −5° C. precipitated N,N′ dicyclohexyl urea is filtered off, the filtrate evaporated, dissolved in 100 ml acetone, allowed to stand overnight at −8° C. and residual N,N′-dicyclohexyl urea filtered off. Evaporation of the filtrate gives 14.1 g oily (+)-threo-5-[N-benzyloxycarbonylglycyloxy-(2-chlorophenyl)-methyl]-4-methoxy-2(5H)-furanone.

The latter is dissolved in 300 ml ethyl acetate, mixed with ice cooling with 30 ml 33% hydrobromide solution in glacial acetic acid and allowed to stand for 24 hours. After sucking off the crystallate, washing with ethyl acetate and drying at 105° C. in vacuum 10.29 g (26.2 mmole) of the title compound in the form of the hydrobromide is obtained with m p. 215°–216° C. (decomp ) and TLC-Rf (chloroform/methanol 95/5)=0.18. Yield: 87.4%. $[\alpha]_D^{20}+17.4$ (c=0.5; methanol).

Analysis: $C_{14}H_{14}ClNO_5 \times HBr$ (392.65) calc.: C (42.83), H (3.85), N (3.57) found: C (43.20), H (4.01), N (3.41)

EXAMPLE 152

(+)-threo-5-[2-chlorophenyl-(N-pivaloylglycyloxy)-methyl]-4-methoxy-2(5H)-furanone To the solution of 2.22 g (15 mmole) 4-pyrrolidinopyridine and 4.0 ml (50 mmole) pyridine in 100 ml anhydrous dichloromethane, with stirring and cooling to 0° C., are added in succession 5.89 g (15 mmole) (+)-theo-5[2-chlorophenyl-(glycyloxy)-methyl]-4-methoxy-2(5H)-furanone hydrobromide (for preparation see Example 151) and 2.0 ml (16 mmole) pivalic acid chloride, then stirring for 4 hours at 0° C. This is then washed free of pyridine and 4-pyrrolidinopyridine with ice water and 0.1M hydrochloric acid, the dichloromethane phase dried over anhydrous sodium sulfate, evaporated and crystallized from tert. butylmethyl ether/n-pentane. After drying at 70° C. in vacuum recrystallization from tert. butylmethyl ether gives 4.3 g (10.9 mmole) of the title compound with m.p. 100°–102° C. and TLC-Rf (chloroform/methanol 95/5)=0.42. Yield: 72%. $[\alpha]_D^{20}+22.6$ (c=0.5; methanol).

Analysis: $C_{19}H_{22}ClNO_6$ (395.85) calc.: C (57.65), H (5.60), N (3.54), Cl (8.96) found: C (57.85), H (5.81), N (3.58), Cl (9.3).

EXAMPLE 153

(−)-threo-5-2-chlorophenyl-(glycyloxy)-methyl]-4-methoxy-2(5H)-furanone-hydrobromide Preparation analogous to Example 151 by esterification of (−)-threo-5-(2-chlorophenylhydroxymethyl)-4-methoxy-2(5H)-furanone (for preparation see Example 144) with N-benzyloxycarbonylglycine and subsequent splitting off of the protective group by means of HBr/glacial acetic acid in ethyl acetate. Recrystallization from ethanol gives the title compound with m.p. 225°–226° C. (decomp.) and TLC-Rf (chloroform/methanol 95/5)=0.18. Yield: 69%. $[\alpha]_D^{20} -17.8$ (c=1; methanol).

Analysis: $C_{14}H_{14}ClNO_5 \times HBr$ (392.65) calc.: C(42.83), H(3.85), N(3.57), Br(20.35), Cl(9.03) found: C(42.68), H(3.78), N(3.48), Br(19.8), Cl(9.1)

EXAMPLE 154 threo-5-[N-(tert. butoxycarbonyl)-2-methylalanyloxy-(2-chlorophenyl)-methyl]-4-methoxy-2(5H)-furanone Preparation by esterification of threo-5-(2-chlorophenylhydroxymethyl)-4-methoxy-2(5H)-furanone with N-tert.butoxycarbonyl-2-methylalanine. m.p. 192°–195° C. (from methanol). TLC-Rf (chloroform/methanol 95/5)=0.58.

Analysis: $C_{21}H_{26}ClNO_7$ (439.90) calc.: C(57.34), H(5.96), N(3.18), Cl(8.06) found: C(57.24), H(5.72), N(3.15), Cl(8.0)

EXAMPLE 155 threo-5-[2-chlorophenyl-(2-methylalanyloxy)-methyl]-4-methoxy-2(5H)-furanone-hydrobromide Preparation by splitting off of the protective group from the substance of Example 154 by means of HBr/glacial acetic acid. m.p. 177°–181° C. (from acetone). TLC-Rf (chloroform/methanol 6/4)=0.6. Yield: 65%.

Analysis: $C_{16}H_{18}ClNO_5 \times HBr$ (420.70). calc.: C(45.68), H(4.55), N(3.33), Br(18.99), Cl(8.43) found: C(44.65), H(4.42), N(3.18), Br(18.9), Cl(9.0)

EXAMPLE 156 threo-5-[1-(N-benzyloxycarbonylamino)-1-cyclohexylcarbonyloxy-(2-chlorophenyl)-methyl]-4-methoxy-2(5H)-furanone Preparation by esterification of threo-5-(2-chlorophenylhydroxymethyl)-4-methoxy-2(5H)-furanone with 1-(N-benzyloxycarbonylamino)-1-cyclohexane carboxylic acid. m.p. 151°–153° C. (from isopropanol). TLC-Rf (chloroform/methanol 9/1)=0.6. Yield: 54.6%.

Analysis: $C_{27}H_{28}ClNO_7$ (513.98) calc.: C(63.10), H(5.49), N(2.73), Cl(6.90) found: C(63.11), H(5.49), N(2.72), Cl(7.1)

The 1-(N-benzyloxycarbonylamino)-1-cyclohexane carboxylic acid used for esterification was obtained by reacting 1-amino-1-cyclohexane carboxylic acid with chloroformic acid benzyl ester in the presence of NaOH-solution. m.p. 151°–154° C. (from trichloroethylene).

EXAMPLE 157 threo-5-[1-amino-1-cyclohexylcarbonyloxy-(2-chlorophenyl)-methyl]-4-methoxy-2(5H)-furanone hydrobromide Preparation by splitting off of the protective group from the substance of Example 156 by means of HBr/glacial acetic acid in ethyl acetate and recrystallization from isopropanol. m.p. 196°–197° C. TLC-Rf (chloroform/methanol 98/2)=0.45. Yield: 71.9%.

Analysis: $C_{19}H_{22}ClNO_5 \times HBr$ (460.76) calc.: C(49.53), H(5.03), N(3.04), Br(17.34), Cl(7.69) found: C(49.45), H(5.05), N(3.03), Br(16.9), Cl(7.9)

Examples for the preparation of pharmaceutical compositions of the substances according to the invention.

A. Tablets:

For the production of tablets each of 250 mg individual weight containing 5 to 100 mg active substance, depending on the desired activity strength, the following are required:

| | |
|---|---|
| substance according to the invention | 200 to 4000 g |
| cellulose powder | 2000 g |
| maize starch | 1200 g |
| colloidal silicic acid | 80 g |
| magnesium stearate | 20 g |
| milk sugar | ad 10000 g |

The active substance and auxiliary substances are homogeneously mixed and compacted in the usual manner to tablets each of 250 mg weight and 9 mm diameter. If desired the tablets are provided with a film coating.

B. Capsules:

For the production of capsules containing 5 to 100 mg depending on the desired strength the following are required:

| | |
|---|---|
| substance according to the invention | 500 to 10000 g |
| maize starch | 2000 g |
| colloidal silicic acid | 300 g |
| magnesium stearate | 50 g |
| cellulose powder | ad 20000 g |

The finely powdered materials are homogeneously mixed and filled into hard gelatin capsules of size 2 in an amount of 200 mg pro capsule.

C. Juice:

For the production of a juice containing 0.035 to 0.7% by weight active product, depending on the desired activity strength, the following are required:

| | |
|---|---|
| substance according to the invention | 35 to 700 g |
| propylene glycol | 20000 g |
| glycerol | 20000 g |
| methyl cellulose | 1000 g |
| sodium cyclamate | 500 g |
| saccharin sodium | 50 g |
| demineralized water | ad 100000 g |

The active material is finely ground and stirred homogeneously into the solution of the auxiliary materials.

D. Suppository:

For the production of suppositories each of 3 g individual weight, containing 5 to 100 mg of active material per suppository, depending on the desired activity strength, the following are required:

| | |
|---|---|
| substance according to the invention | 50 to 1000 g |
| colloidal silicic acid | 60 g |
| lecithin | 150 g |
| hard fat | ad 30000 g |

The finely ground active material is homogenously stirred into a melt of the auxiliary substances and cast into suppositories of 3 g individual weight.

For the determination of the anticonvulsive/antiepileptic activity of the substances according to the present invention the method described by E. A. Swinyard et al., J. Pharmacol. exp. Therapeut. 106, 319–330

(1952) and by L. A. Woodbury et al., Arch. int. Pharmacodyn., 92, 97–107 (1952) was used. To male mice (NMRI) with a body weight of 20–25 g via corneal electrodes, an alternating current of 50 Hz and 50 mA is applied for 0.2 sec. (HSE-shock stimulation apparatus; type 207). The maximum electroshock spasm (MES) consists of a tonic extension of the rear extremities, the clonic twitch and loss of consciousness. The activity criterion is taken as being the inhibition of the extensor spasm by the substances according to the present invention. Before the experiments the mice had free access to feed and water. The test substances were administered orally as suspensions in 0.2% agar by stomach tubes; the control animals received adequate volumes of agar. 1 hour and 3 hours after administration the test for protective action against MES was carried out.

In following Table 4 the results of the MES test with dosages of 50 to 100 mg of the substances according to the invention per kg of body weight are given in comparison with conventional anti-epileptics. As percentage action the percentage proportion of those animals which in the MES test were protected 100% against the extensor spasm is given. 10 animals were used per test.

In table 4, as ED 50 values the dosages of the substances according to the invention and of conventional anti-epileptics are given which in the MES test were able to protect 50% of the animals completely from the extensor spasm 1 hour after administration. The ED 50 values were determined according to Lichtfield and Wilcoxon J. Pharmacol. exp. Therapeut. 96, 99 (1949) in each case with 4 to 5 animal groups each of 8–10 animals per dosage stage.

The ED 50 values marked * are estimated values derived from several tests with different dosages.

During the experiments described above, the animals were observed during the whole of the experimental period (up to 4 hours) for signs of substance-caused changes of behaviour and neurotoxicity (motility, muscle tonus, respiratory frequency, body temperature and general behaviour). Up to a dosage of 100 mg/kg, in the case of all the tested compounds, no neurotoxic symptoms were ascertained. In comparison hereto, Table 5 sets out the lower limiting dosages of conventional anticonvulsives which, after oral administration, bring about neurotoxicity symptoms in mice.

With all the compounds according to the invention in dosages up to 300 mg/kg administered orally no mortality whatever of the mice was observed.

The present investigations show in effect a good anticonvulsive activity and excellent therapeutic breadth of the compounds according to the invention.

TABLE 4

| Substance according to Example No. | Results of the MES test (n = 10) | | | ED 50 values [mg/kg] |
|---|---|---|---|---|
| | dose [mg/kg] | protective action [%] after | | |
| | | 1 hr | 3 hrs | |
| 103 A | 100 | 100 | 100 | 10.7 |
| 103 B | 100 | 50 | 0 | 95 |
| 104 A | 50 | 100 | 100 | |
| 104 B | 100 | 60 | 0 | 105 |
| 105 | 100 | 70 | 0 | 87.5 |
| 106 | 50 | 100 | 70 | 23.1 |
| 107 A | 100 | 100 | 60 | 10–15* |
| 108 A | 100 | 90 | 0 | 70–80* |
| 110 A | 100 | 100 | 0 | 40–50* |
| 111 | 50 | 100 | 80 | 24.2 |
| 112 | 50 | 100 | 70 | 22.2 |
| 113 | 50 | 100 | 50 | 25–35* |
| 114 | 50 | 100 | 30 | 40.0 |

TABLE 4-continued

| Substance according to Example No. | Results of the MES test (n = 10) | | | ED 50 values [mg/kg] |
|---|---|---|---|---|
| | dose [mg/kg] | protective action [%] after | | |
| | | 1 hr | 3 hrs | |
| 115 | 100 | 100 | 100 | 30–40* |
| 117 A | 50 | 100 | 100 | 16 |
| 117 B | 50 | 90 | 0 | 25.3 |
| 119 B | 50 | 100 | 20 | 37.6 |
| 121 A | 50 | 100 | 90 | |
| 122 A | 50 | 100 | 100 | 15–20* |
| 123 A | 50 | 70 | 20 | |
| 124 A | 100 | 100 | 20 | 25–35* |
| 125 A | 50 | 100 | 80 | |
| 127 A | 50 | 100 | 100 | |
| 129 A | 100 | 100 | 100 | 40–50* |
| 129 B | 100 | 50 | 0 | 95–105* |
| 130 | 100 | 100 | 100 | 40–50* |
| 131 | 100 | 100 | 100 | 54.5 |
| 132 | 100 | 20 | 50 | |
| 133 | 100 | 100 | 100 | 60–70* |
| 135 A | 100 | 100 | 100 | 65–75* |
| 136 A | 50 | 60 | 50 | 40–50* |
| 137 A | 50 | 100 | 100 | |
| 138 A | 100 | 30 | 20 | |
| 139 A | 50 | 100 | 50 | 15–20* |
| 139 B | 100 | 40 | 10 | |
| 141 A | 100 | 40 | 10 | 110–120* |
| 150 | 50 | 100 | 100 | 14.4 |
| 151 | 50 | 100 | 100 | 12.2 |
| 152 | 50 | 100 | 90 | 16.3 |
| 153 | 100 | 40 | 0 | |
| 155 | 25 | 50 | 10 | 20–30* |
| 157 | 100 | 100 | 40 | 27.5 |
| carbamazepine | 50 | 100 | 100 | 14.6 |
| diazepam | 50 | 100 | 100 | 13.8 |
| phenytoin | 50 | 100 | 100 | 9.1 |
| ethosuximide | 100 | 0 | 0 | >250** |
| phenobarbital | 100 | 100 | 100 | 19.2 |
| Valproic Acid$_{(ip)}$ | 100 | 0 | 0 | 205 |

*estimated values
**4 hours after administration

TABLE 5

| Neurotoxic limiting dose in the mouse | |
|---|---|
| substance | dose p.o. [mg/kg] |
| carbamazepine | 100 |
| diazepam | 40 |
| diphenylhydantoin | 100 |
| ethosuximide | 500 |
| pentobarbital | 60 |
| phenobarbital | 60 |
| valproic acid | 350 |
| compound according to the invention | all > 100 |

We claim:

1. Amino acid esters of the formula I

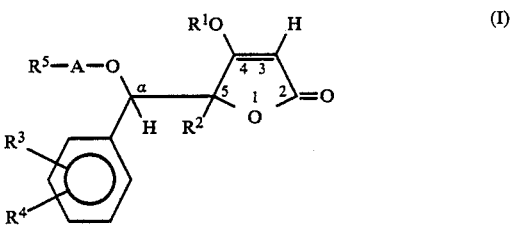

(I)

wherein the oxygen atoms at C-5 and C-α assume relative to each other the threo position and wherein
$R^1$ is a methyl or ethyl group;
$R^2$ is a hydrogen atom or a methyl group, $R^3$ and $R^4$ are independently from each other a hydrogen, fluorine, chlorine or bromine atom, a lower alkyl group having 1 to 3 C atoms, a perfluoro lower alkyl having 1 to 3 C atoms, the difluoromethoxy or nitro group, A is the acyl radical of one of the following amino acids:
alanine, leucine, isoleucine, norleucine, valine, norvaline, phenylglycine, phenylalanine, proline, 5-oxoproline, glutamic acid, glutamine, asparaginic acid, asparagine, methionine, glycine, β-alanine, 4-aminobutyric acid, 2-methylalanine or a 1-amino-1-cycloalkane carboxylic acid having a 3–7-member cycloalkyl radical, in each case a hydrogen atom of the amino group of said amino acids being replaced by the radical $R^5$, and $R^5$ is a hydrogen atom, a lower alkanoyl radical having 2 to 5 C atoms, the benzyloxycarbonyl radical (Z) or the tert. butoxycarbonyl radical (BOC), and pharmacologically compatible (acceptable) acid addition salts thereof.

2. Amino acid esters according to claim 1 in the form of the racemates thereof.

3. Amino acid esters according to claim 1 in the form of the enantiomers thereof or in the form of enantiomer mixtures.

4. Amino acid esters according to claim 1 in the form of the diastereomers thereof or in the form of diastereomer mixtures.

5. Amino acid esters according to any one of claims 1 to 4, characterized in that one of the radicals $R^3$ or $R^4$ is a hydrogen atom and the other a fluorine, chlorine or bromine atom located in 2'-position or a methyl or trifluoromethyl group located in 2'-position.

6. Amino acid esters according to any one of claims 1 to 4, characterized in that one of the two radicals $R^3$ or $R^4$ is a fluorine, chlorine or bromine atom located in 2'-position or a trifluoromethyl group located in 2'-position and the other is a chlorine or bromine atom or a trifluoromethyl group, respectively in 4', 5' or 6'-position.

7. Amino acid esters according to any one of claims 1 to 6, characterized in that the alcoholic component thereof formed by the threo-5-arylhydroxymethyl-2-(5H)-furanone radical is optically dextrorotary, considered on its own.

8. Pharmaceutical preparation comprising a pharmacological acceptable carrier and one or more of the compounds according to any one of claims 1 to 7.

* * * * *